United States Patent
Li et al.

(10) Patent No.: US 7,189,341 B2
(45) Date of Patent: Mar. 13, 2007

(54) ELECTROCHEMICAL SENSOR INK COMPOSITIONS, ELECTRODES, AND USES THEREOF

(75) Inventors: Huawen Li, Camarillo, CA (US); Michael J. Tierney, San Jose, CA (US)

(73) Assignee: Animas Technologies, LLC, West Chester, PA (US)

( * ) Notice: Subject to any disclaimer, the term of this patent is extended or adjusted under 35 U.S.C. 154(b) by 442 days.

(21) Appl. No.: 10/692,761

(22) Filed: Oct. 24, 2003

(65) Prior Publication Data

US 2005/0036020 A1     Feb. 17, 2005

Related U.S. Application Data

(60) Provisional application No. 60/495,470, filed on Aug. 15, 2003.

(51) Int. Cl.
*H01B 1/22* (2006.01)
*C25B 11/04* (2006.01)
*G01N 27/327* (2006.01)

(52) U.S. Cl. .................. 252/511; 252/500; 252/514; 252/182.1; 106/1.18; 106/1.21; 106/1.22; 106/1.23; 106/1.24; 106/31.64; 106/31.92; 204/291; 204/292; 204/293; 204/294; 204/403.15; 205/777.5; 205/794.5; 600/345; 600/347; 600/364

(58) Field of Classification Search ........... 242/511, 242/514, 520.3, 502; 106/31.92, 31.64; 204/292–294, 204/403.15; 205/794.5; 600/347
See application file for complete search history.

(56) References Cited

U.S. PATENT DOCUMENTS

| | | | |
|---|---|---|---|
| 3,173,885 A | 3/1965 | Short et al. | |
| 3,457,113 A | 7/1969 | Diebert | |
| 4,374,670 A * | 2/1983 | Slocombe | 522/33 |
| 4,871,797 A * | 10/1989 | Buter | 524/505 |
| 4,933,062 A | 6/1990 | Shaw et al. | |
| 5,174,925 A * | 12/1992 | Fujii et al. | 252/514 |
| 5,231,028 A | 7/1993 | Mullen | |
| 5,653,918 A | 8/1997 | Towlson | |
| 5,776,372 A | 7/1998 | Saito et al. | |
| 5,795,453 A | 8/1998 | Gilmartin | |
| 5,851,438 A | 12/1998 | Chan | |
| 5,928,571 A | 7/1999 | Chan | |
| 6,042,751 A * | 3/2000 | Chan et al. | 252/511 |
| 6,309,535 B1 | 10/2001 | Williams | |
| 6,587,705 B1 | 7/2003 | Kim et al. | |
| 6,599,408 B1 | 7/2003 | Chan et al. | |
| 6,627,058 B1 * | 9/2003 | Chan | 204/403.15 |

FOREIGN PATENT DOCUMENTS

| | | |
|---|---|---|
| EP | 0 987 333 | 3/2000 |
| EP | 0 942 278 B1 | 6/2002 |
| GB | 2 335 278 A | 9/1999 |

OTHER PUBLICATIONS

Alegret, S., et al, "Carbon-Polymer Biocomposites for Amperometric Sensing," *Biosensors & Bioelectronics*, 11:1/2 35-44 (1996).

* cited by examiner

*Primary Examiner*—Mark Kopec
*Assistant Examiner*—Kallambella Vijayakumar
(74) *Attorney, Agent, or Firm*—RatnerPrestia

(57) ABSTRACT

The invention is directed to conductive polymer compositions, catalytic ink compositions (e.g., for use in screen-printing), electrodes produced by deposition of an ink composition, as well as methods of making, and methods of using such compositions and electrodes. An exemplary ink material comprises a metal catalyst (e.g., platinum black and/or platinum-on-carbon), graphite as a conducting material, a polymer binding material, and an organic solvent. In one aspect, the polymer binding material comprises a polymer binder blend comprising first and second polymers, wherein the first polymer has a glass transition temperature higher than the second polymer. In a second aspect, the polymer binding material comprises a hydrophilic acrylic polymer, copolymer, or terpolymer. The conductive polymer compositions of the present invention may be used, for example, to make electrochemical sensors. Such sensors may be used, for example, in a variety of devices to monitor analyte amount or concentrations in subjects.

21 Claims, No Drawings

ELECTROCHEMICAL SENSOR INK COMPOSITIONS, ELECTRODES, AND USES THEREOF

CROSS-REFERENCE TO RELATED APPLICATIONS

This application claims the benefit of U.S. Provisional Patent Application Ser. No. 60/495,470 filed 15 Aug. 2003, which application is incorporated herein by reference in its entirety.

This invention was made with U.S. Government support under Grant No. R44 DK56544 awarded by the National Institute of Diabetes and Digestive and Kidney Diseases of the National Institutes of Health. Accordingly, the U.S. Government may have certain rights in this invention.

TECHNICAL FIELD

The present invention relates generally to conductive polymer film compositions and inks used, for example, in the manufacturing of medical electrodes.

BACKGROUND OF THE INVENTION

Numerous systems for monitoring an analyte amount or concentration in a subject are known in the art, including, but not limited to the following: U.S. Pat. Nos. 5,279,543, 5,362,307, 5,569,186, 5,695,623, 5,713,353, 5,730,714, 5,735,273, 5,771,890, 5,791,344, 5,827,183, 5,840,020, 5,885,211, 5,903,373, 5,954,685, 5,989,409, 5,995,860, 6,022,316, 6,023,629, 6,026,314, 6,044,285, 6,113,537, 6,141,573, 6,142,939, 6,144,869, 6,175,752, 6,180,416, 6,188,648, 6,201,979, 6,233,471, 6,272,364, 6,298,254, 6,299,578, 6,309,351, 6,326,160, 6,360,888, 6,477,395, 6,491,657, 6,512,939, 6,520,326, 6,529,755, 6,560,471, 6,561,978, 6,565,509, 6,576,101, 6,579,690, 6,587,705, and 6,615,078. Many devices used for monitoring of analyte levels in a subject use sensing electrodes. These electrodes are typically produced by thick film deposition of an ink material.

The ink material may comprise graphite as a conducting material, a polymer binding material, and an organic solvent. Ink material may further comprise platinum black and/or platinum-on-carbon as the catalyst. U.S. Pat. No. 6,042,751 pertains to a conductor composition of up to 5% platinum powders and/or platinum deposited on graphite, modified graphite and a thermoplastic polymer such as the styrene-containing acrylic copolymers poly(styrene-acrylonitrile). U.S. Pat. No. 6,309,535 pertains to an electrode consisting of graphite particles coated with a transition metal catalyst, carbon particles, and a binder that is a vinyl chloride/vinyl acetate copolymer.

U.S. Pat. No. 5,928,571 discloses a conductive composition for iontophoretic electrodes containing silver particles, silver chloride particles, carbon and graphite as the conducting material, and a copolymer of hydrophilic and hydrophobic monomers. The hydrophobic monomers can be styrene, and the hydrophilic monomers can be acrylates.

EP 0 942 278 B1 discloses a sampling system for monitoring the concentration of an analyte present in a biological system, comprising a sensor element in operative contact with a reservoir, wherein the sensor element reacts electrochemically with hydrogen peroxide produced in the reservoir to provide a detectable signal, characterised in that the sensor element comprises an electrode having a geometric surface area which ranges from 0.1 to 3 cm$^2$, a background current which ranges from 2 to 60 nanoamps (nA) or less when measured in a buffer solution at 0.6V, and a sensitivity which ranges from 6 to 180 nA/μM of hydrogen peroxide when measured in a buffer solution at 0.6V.

The present invention provides methods and compositions for improving performance of analyte monitoring systems that employ sensing electrodes comprising the conductive compositions of the present invention.

SUMMARY OF THE INVENTION

The present invention relates to conductive polymer compositions, ink formulation compositions (e.g., a catalytic screen-printing ink, an electrode ink formulation), electrodes produced using the compositions of the present invention, as well as methods of making and using the compositions and electrodes of the present invention.

In one aspect, the present invention relates to a conductive polymer composition comprising about 0.01% to about 5% by weight of a transition metal catalyst. The composition further comprises an electrically conductive material, and a polymer binder blend comprising a first polymer or first polymer mixture, wherein the first polymer or polymers comprising the first polymer mixture have characteristic glass transition temperatures, and a second polymer having a characteristic Tg, wherein the Tg of the first polymer or at least one of the polymers comprising the first polymer mixture is higher than the Tg of the second polymer. In a preferred embodiment, when the first polymer, or any polymer of the first polymer mixture, and the second polymer are the same copolymer but with different molecular weights, neither (i) the first polymer or any polymer of the first polymer mixture nor (ii) the second polymer comprise styrene, alkyl styrene, cycloaklystyrene or hydroxystyrene monomers.

In one embodiment, the polymer binder blend may consist essentially of the first polymer and the second polymer. In another embodiment, the polymer binder blend may consist essentially of two polymers in a first polymer mixture and a second polymer.

In some embodiments, the second polymer is an acrylic polymer, copolymer, or terpolymer. The acrylic polymer, copolymer, or terpolymer in preferred embodiments is hydrophilic.

Exemplary first polymers (or polymers comprising the first polymer mixture) include, but are not limited to, are selected from the group consisting of poly (methyl methacrylate), PMMA; poly (styrene methyl methacrylate), PSMMA; poly (styrene acylonitrile), SAN; poly (acylonitrile butadiene styrene), ABS; and other thermoplastic polymers.

Exemplary second polymers include, but are not limited to, polymers selected from the group consisting of poly (methyl methacrylate), PMMA; poly (styrene methyl methacrylate), PSMMA; poly (styrene acylonitrile), SAN; poly (acylonitrile butadiene styrene), ABS; and other thermoplastic polymers.

In one embodiment, the polymer binder blend comprises a first polymer mixture and the second polymer comprises an acrylic polymer, copolymer, or terpolymer. The acrylic polymer, copolymer, or terpolymer may be hydrophilic. Further, it may comprise acrylic acid monomers that comprise additional hydrophilic functional groups on the α-carbon of the acrylic acid backbone, β-carbon of the acrylic acid backbone, and/or the pendant carboxyl-group on the α-carbon of the acrylic acid backbone.

The transition metal catalyst may be selected from the platinum-group metals, including, but not limited to platinum (Pt), palladium, and rhodium. The catalyst may also, for example, be platinum on graphite. The conductive material may be synthetic graphite, pyrolytic graphite, or natural graphite.

In a second aspect, the present invention relates to a conductive polymer composition comprising, about 0.01% to about 5% by weight of a transition metal catalyst. The composition further comprises an electrically conductive material, and a polymer binder comprising a hydrophilic, acrylic polymer, copolymer, or terpolymer. In a preferred embodiment, the hydrophilic, acrylic polymer, copolymer, or terpolymer comprises acrylic acid monomers that comprise additional hydrophilic functional groups on the $\alpha$-carbon of the acrylic acid backbone, $\beta$-carbon of the acrylic acid backbone, and/or the pendant carboxyl-group on the $\alpha$-acarbon of the acrylic acid backbone. Transition metal catalysts (e.g., platinum-group, and platinum on graphite) and conductive materials (e.g., graphite), as described herein and above, may be used in the conductive polymer composition.

In some embodiments, the hydrophilic, acrylic copolymer or terpolymer comprises acrylate and/or alkylacrylate monomers comprising functional groups selected from the group consisting of amino, hydroxy, and carboxy. The copolymer or terpolymer may comprise, for example, about 0% to about 99% weight, based on the total weight of the copolymer or terpolymer, of moieties resulting from the polymerization of monomers comprising the functional groups with other monomers free of hydroxy, carboxy, and amino functional groups to form copolymers or terpolymers.

The present invention further comprises electrodes, comprising the above described conductive polymer compositions typically on a non-conducting substrate.

These and other embodiments of the present invention will readily occur to those of ordinary skill in the art in view of the disclosure herein.

DETAILED DESCRIPTION OF THE INVENTION

All publications, patents and patent applications cited herein are hereby incorporated by reference in their entireties.

1.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "an electrode" includes a combination of two or more such electrodes, reference to "an analyte" includes mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also comprise memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Santa Clara, Calif.; and, National Semiconductor, Santa Clara, Calif.

The terms "analyte" and "target analyte" are used to denote any one or more physiological analytes of interest that are, for example, one or more specific substance, component, or combinations thereof that one is desirous of detecting and/or measuring in a chemical, physical, enzymatic, optical analysis, or combinations thereof. In the present invention, analytes are typically detected using methods comprising the sensors of the present invention. Suitable sensor electrodes can be made that comprise the conductive polymer compositions of the present invention. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a substance that has a physiological action, for example, a drug or pharmacological agent. In order to facilitate detection of certain analytes, an enzyme (or enzymes) can be associated with, for example, a sensing electrode. The selected enzyme(s) are typically capable of catalyzing a reaction with the analyte to the extent that a product of this reaction can be sensed, e.g., can be detected electrochemically from the generation of a current which current is detectable and proportional to the amount of the analyte which is reacted. Analytes in non-biological systems may also be evaluated using the compositions and methods of the present invention.

A "sampling device," "sampling mechanism" or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., International Publication No. WO 91/12772, published 5 Sep. 1991; U.S. Pat. Nos. 5,636,632, 6,491,657, 6,234,990, 6,190,315), suction, electroporation, thermal poration, passive diffusion (see, e.g., International Publication Nos.: WO 97/38126 (published 16 Oct. 1997); WO 97/42888, WO 97/42886, WO 97/42885, and WO 97/42882 (all published 20 Nov. 1997); and WO 97/43962 (published 27 Nov. 1997)), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88-93; International Publication WO 99/44507, published 1999 Sep. 10; International Publication WO 99/44638, published 1999 Sep. 10; and International Publication WO 99/40848, published 1999 Aug. 19). Iontophoretic sampling devices are described, for example, in International Publication No. WO 97/24059, published 10 Jul. 1997; European Patent Application EP 0 942 278 B1, published 15 Sep. 1999; International Publication No. WO 96/00110, published 4 Jan. 1996; International Publication No. WO 97/10499, published 2 Mar. 1997; U.S. Pat. Nos. 5,279,543; 5,362,307; 5,730,714; 5,771,890; 5,989,409; 5,735,273; 5,827,183; 5,954,685 and 6,023,629. Further, a polymeric membrane may be used at, for example, the electrode surface to block or inhibit access of interfering species to the reactive surface of the electrode.

The term "physiological fluid" refers to any desired fluid to be sampled, and includes, but is not limited to, tears, blood, cerebrospinal fluid, interstitial fluid, semen, perspiration (sweat), saliva, urine and the like.

The term "artificial membrane" or "artificial surface," refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system" or "analyte monitoring device" refers to a system useful for obtaining frequent measurements of a physiological analyte present in a biological system. Such a system may comprise, but is not limited to, a sensing mechanism and a microprocessor mechanism in operative communication with the sensing mechanism. Such a monitoring system may further comprise a sampling mechanism. In this case the sampling mechanism is also typically in operative communication with the microprocessor. The GlucoWatch® (Cygnus, Inc., Redwood City, Calif.) biographer and the GlucoWatch® G2™ (Cygnus, Inc., Redwood City, Calif.) biographer are examples of analyte monitoring systems (see, for example, Tamada, J A, et al., Nature Medicine 1:1198–1201 (1995); Rao, G, et al., Pharmaceutical Research 12:1322–1326 (1995); Guy, R H, et al., Diabetes, Nutrition and Metabolism 9:42–46 (1996); Kurnik, R T, et al., J. Electrochemical Soc. 145:4119 (1998); Kurnik, R T, et al., Sensors and Actuators, 60:19 (1999); Chan, M S, et al., Clinical Chemistry, 45:1689 (1999); Uhegbu, C, et al., Clinical Chemistry, 45:1679 (1999); Tierney, M J, et al., Clinical Chemistry, 45:1681–83(1999); Tamada, J A, et al., Journal of the American Medical Association, 282:1839 (1999); Tierney, M J, et al., Electroanalysis 12: 666 (2000)). Other examples of analyte monitoring systems include, but are not limited to, microporation (e.g., U.S. Pat. Nos. 5,885,211, 5,903,373), ultrasound permeation/extraction/detection (e.g., U.S. Pat. No. 6,491, 657), and implantable monitoring systems (e.g., U.S. Pat. Nos. 6,579,690, 6,576,101, 6,565,509, 6,560,471, 6,512, 939, 6,477,395, 6,360,888, 6,022,316, 6,175,752, 5,885,211, 5,569,186).

The term "frequent measurement" refers to a series of two or more measurements obtained from a particular biological system, which measurements are obtained using a device maintained in operative contact with the biological system over a time period in which a series of measurements (e.g., second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, e.g., stratum corneum, or mucosal tissue.

The term "transdermal extraction," or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, microfine lances, microfine cannulas, subcutaneous implants or insertions, combinations thereof, and the like.

The term "sensing device," or "sensing mechanism," encompasses any device that can be used to measure the concentration or amount of an analyte, or derivative thereof, of interest. Preferred sensing devices for detecting blood analytes generally include electrochemical devices, optical and chemical devices and combinations thereof. In the context of the present invention, preferred sensing devices employ electrochemical detection using electrodes comprising the electrochemical inks of the present invention. Examples of electrochemical devices include the Clark electrode system (see, e.g., Updike, et al., (1967) Nature 214:986–988), and other amperometric, coulometric, or potentiometric electrochemical devices. Other sensing device include, but are not limited to, those using optical methods, for example UV detection or infrared detection (e.g., U.S. Pat. Nos. 5,747,806, 5,267,152, 5,086,229, 5,747, 806, and 4,975,581).

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface that converts the analyte, or a derivative thereof, to electrical signal. Some catalytic materials, membranes, and fabrication technologies are described by Newman, J. D., et al. (1995) Analytical Chemistry 67:4594–4599. New electrochemical ink compositions useful for producing biosensor electrodes are described herein.

The "sensor element" can comprise components in addition to the sensing electrode, for example, it can include a "reference electrode" and a "counter electrode." The term "reference electrode" is used to mean an electrode that provides a reference potential, e.g., a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode that is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface," and "reactive face" are used interchangeably herein to mean the surface of the sensing electrode that: (1) may be in contact with the surface of an ionically conductive material that comprises an analyte or through which an analyte, or a derivative thereof, flows from a source thereof; (2) is comprised of a catalytic material (e.g., platinum-group metals (including, platinum, palladium, rhodium, ruthenium, osmium, and iridium), nickel, copper, and silver, as well as, oxides, and dioxides, thereof, and combinations or alloys of the foregoing, which may comprise carbon as well) or a material that provides sites for electrochemical reaction; (3) converts a chemical signal (for example, hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal when an appropriate electrical bias is supplied, that is correlatable with an amount or concentration of analyte.

The term "buffer" refers to one or more components that are added to a composition in order to adjust or maintain the pH of the composition.

The term "electrolyte" refers to a component (e.g., salts or buffer components) of an ionically conductive medium that allows an ionic current to flow within the medium.

The term "collection reservoir" is used to describe any suitable containment method or device for containing a sample from a biological system. For example, the collection reservoir can be a receptacle containing a material that is ionically conductive, or alternatively it can be a material, such as a hydrophilic polymer. Such collection reservoirs can be in the form of a sponge, porous material, or hydrogel (for example, in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths. A collection reservoir, for example, be used in a monitoring device that extracts a sample for detection of analyte. The analyte is typically extracted into a collection reservoir that is in contact with a sensing device, e.g., a sensing electrode.

The term "support tray" typically refers to a rigid, substantially planar platform and is used to support an electrode assembly. The support tray may also be used, for example, to support a collection assembly (e.g., comprising one or more collection reservoirs) and/or align an electrode assembly with a collection assembly. The support tray provides one way of placing an electrode assembly and a collection assembly into a sampling system.

The terms "about" or "approximately" when associated with a numeric value refers to that numeric value plus or minus 10% of the unit of measure (e.g., percent, grams, degrees or volts).

By the term "printed" is meant a substantially uniform deposition of a conductive polymer composite film (e.g., an electrode ink formulation) onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, electroplating, laminating, or the like. See, for example, Polymer Thick Film, by Ken Gilleo, N.Y.:Van Nostrand Reinhold, 1996, pages 171–185.

The term "physiological effect" encompasses effects produced in the subject that achieve the intended purpose of a therapy.

"Decay" refers to a gradual reduction in the magnitude of a quantity, for example, a current detected using a sensor electrode where the current is correlated to the concentration of a particular analyte and where the detected current gradually reduces but the concentration of the analyte does not.

The term "glass transition temperature" or "Tg" as used herein refers to the temperature at which an amorphous material (such as a polymer) changes from a brittle vitreous state to a plastic state. Many polymers, for example acrylics, and their derivatives have this transition point. The Tg typically depends on the polymer composition and extent of annealing. In the context of the present invention, a high Tg polymer has a high Tg relative to that of a second polymer, that is, a low Tg polymer. The terms high Tg and low Tg are used relative to each other.

The term "alkyl" as used herein refers to a straight, branched, or cyclic hydrocarbon chain fragment containing between about one and about twenty carbon atoms, more preferably between about one and about eight carbon atoms, for example, methyl, ethyl, n-propyl, iso-propyl, cyclopropyl, n-butyl, iso-butyl, tert-butyl, cyclobutyl, cyclooctyl, and the like. Straight, branched, or cyclic hydrocarbon chains having eight or fewer carbon atoms will also be referred to herein as "lower alkyl." The hydrocarbon chains may further include one or more degrees of unsaturation, i.e., one or more double or triple bonds, as in, for example, vinyl, propargyl, allyl, 2-buten-1-yl, 2-cyclopenten-1-yl, cyclooctene and the like.

The terms "GlucoWatch® biographer" and "GlucoWatch® G2™ biographer" refer to two exemplary devices in a line of GlucoWatch biographer glucose monitoring devices developed and manufactured by Cygnus, Inc., Redwood City, Calif. To accurately measure this small amount of glucose, the GlucoWatch biographers utilize an amperometric biosensor (Tierney, M. J., et al., Clin. Chem. 45, 1681 (1999)). The glucose oxidase (GOx) enzyme in hydrogel disks (where glucose is collected via reverse iontophoresis) catalyzes the reaction of glucose with oxygen to produce gluconic acid and hydrogen peroxide. As glucose enters the hydrogel, it diffuses throughout. The products of the GOx reaction (hydrogen peroxide and gluconic acid) also diffuse throughout the gel. Finally, peroxide is detected at a platinum-containing working electrode in the sensor via an electro-catalytic oxidation reaction ($H_2O_2 \rightarrow O_2 + 2H^+ + 2e^-$) producing measurable electrical current, and regenerating $O_2$. Thus, ideally, for every glucose molecule extracted, two electrons are transferred to the measurement circuit. Integration over time of the resulting electric current leads to the total charge liberated at the electrode, and the latter is correlated to the amount of glucose collected through the skin.

2.0 Conductive Polymer and Ink Compositions of the Present Invention

The invention relates to ink compositions, conductive polymer compositions, conductive polymer film compositions, screen-printing inks, electrodes, electrode sensors, or methods of making or using the same. The conductive polymer compositions can be used in the production of sensor electrodes for use, for example, in analyte monitoring devices. The sensor inks may be used to print electrochemical sensors, for example, by using screen-printing. In a first aspect, the sensor ink compositions comprise, in combination, an electrically conductive material (e.g., graphite), a transition metal catalyst (e.g., which may be selected from the platinum-group metals) as catalytic material (e.g., platinum on graphite), and a polymer binder blend. Alternatively, in a second aspect of the present invention, instead of a polymer binder blend a polymer binder comprising a hydrophilic, acrylic polymer, copolymer, or terpolymer may be used.

The polymer binder blend typically comprises a first polymer (or polymers comprising a first polymer mixture) wherein the first polymer (or at least one of the polymers of the first polymer mixture) has a higher glass transition temperature relative to a second polymer (or polymers comprising a second polymer mixture). The polymer binder blend of the present invention typically comprises thermoplastic polymers. An exemplary molecular weight range for the first polymer (or at least one polymer of the first polymer mixture) is greater than about 100K and less than about 800K. Exemplary ratios of the first polymer (or first polymer mixture) to the second polymer are 99:1 (first polymer: second polymer), based on the total weight of the polymers in the polymer binder blend, to 1:99 (first polymer:second polymer), for example, 90:10, 80:20, 75:25, 60:40, 50:50, 40:60, 25:75, 20:80, 10:90 (first polymer:second polymer), based on the total weight of the polymers in the polymer binder blend. Other ratios of the first polymer (or first polymer mixture) to the second polymer (or second polymer mixture) will be apparent to one of ordinary skill in the art in view of the teachings of the present specification. Example 1 shows exemplary formulations of 50:50 (first polymer:second polymer) and 70:30 (first polymer:second polymer) polymer binder blends.

The first and second polymers can, for example, be the same type of polymers with two different molecular weights, such as poly (methyl methacrylate) with MW=350,000 (Tg=122° C.) as the first polymer, and poly (methyl methacrylate) with MW=150,000 (Tg=114° C.) as the second polymer. With the proviso that when, in a polymer binder blend, the first polymer (or any polymer of the first polymer mixture) and the second polymer are the same copolymer, having different molecular weights, neither the first polymer (or any polymer of the first polymer mixture) nor the second polymer comprise styrene, alkyl styrene, cycloaklystyrene or hydroxystyrene monomers. The two polymers can also be two different types of polymers with different glass transition temperatures.

Exemplary polymers for use in the present invention include, but are not limited to, poly (methyl methacrylate), PMMA; poly (styrene methyl methacrylate), PSMMA; poly (styrene acylonitrile), SAN; poly (acylonitrile butadiene styrene), ABS; and other thermoplastic polymers.

Experiments performed in support of the present invention demonstrate that PMMA has good binding power. PMMA is readily soluble in ethylene glycol diacetate and electrochemically inert in the range of electrical potentials useful in many analyte monitoring device (e.g., the Gluco-Watch biographer family of monitoring devices). PMMA is available at a number of different molecular weights from a number of vendors (e.g., Atofina Chemicals, Philadelphia, Pa.; Cyro Industries, Rockaway, N.J.). Further, the low cost of PMMA is another advantage in the product of sensing electrodes. In one embodiment of the present invention, the ink composition uses a polymer binder blend comprising poly (methyl methacrylate) with high molecular weight or high Tg as the first polymer and poly (methyl methacrylate) with low molecular weight or low Tg as the second polymer.

In another embodiment of the polymer binder blend of the present invention, the ink composition may comprise a first polymer mixture of high and low molecular weight polymers and an acrylic polymer, copolymer, or terpolymer with low glass transition temperature as the second polymer. The low glass transition temperature (low Tg) second polymer has a low Tg relative to at least one of the polymers of the first polymer mixture. The low glass transition temperature second polymer can be chosen, for example, from hydrophilic acrylic copolymers or terpolymers having functional group selected from, but not limited to, the following: acrylic acid, amino, hydroxy, carboxy, hydroxy and carboxy, hydroxy and amino, amino and carboxy. Such hydrophilic acrylic copolymers or terpolymers may be prepared from monomers having at least one functional group selected from hydroxy, amino and/or carboxy groups. While not wishing to be bound by any particular theory, it appears that by adding more hydrophilic sites to the polymer system, the metal catalyst/graphite (e.g., platinum/graphite) is well exposed on the surface of a sensor (after printing and drying using a polymer system of the present invention) and thus more readily available for catalytic reaction.

The second polymer (e.g., the hydrophilic acrylic copolymer or terpolymer) incorporated into the ink composition may contain from about 0% to about 99% weight, based on the total weight of the second polymer, of moieties resulting from polymerization of monomers having the aforedescribed functional groups with other monomers free of hydroxy, carboxy, and amino functional groups to form copolymers, terpolymers, etc.

In another aspect, the present invention relates use of a polymer binder comprising a hydrophilic, acrylic polymer, copolymer, or terpolymer. These hydrophilic acrylic polymers, copolymers, or terpolymers have similar properties to the hydrophilic acrylic polymers, copolymer and terpolymers described herein above.

In one aspect the present invention relates to compositions comprising between about 0.01% to about 5% (of total weight of the dry composition, i.e., without solvent), preferably about 0.05% to less than 5%, more preferably in the range of about 0.1% to about 2% (of total weight of the dry composition, i.e., without solvent) of one or more transition metal catalysts. The compositions further comprise one or more electrically conductive materials, and a polymer binder blend comprising a first polymer or first polymer mixture, wherein the first polymer or polymers comprising the first polymer mixture have characteristic glass transition temperatures, and a second polymer having a characteristic Tg, wherein the Tg of the first polymer or at least one of the polymers comprising the first polymer mixture is higher than the Tg of said second polymer.

As an alternative to the polymer binder blend, in another aspect of the invention a hydrophilic, acrylic polymer, copolymer, or terpolymer binder is used. In one embodiment, one hydrophilic, acrylic polymer, copolymer, or terpolymer is used as the polymer binder. In a preferred embodiment, the hydrophilic, acrylic polymer, copolymer, or terpolymer comprises acrylic acid monomers that comprise additional hydrophilic functional groups on the α-carbon of the acrylic acid backbone, β-carbon of the acrylic acid backbone, and/or the pendant carboxyl-group on the α-carbon of the acrylic acid backbone.

In one aspect of the present invention, the polymers of the polymer binder blend (or the hydrophilic, acrylic polymer, copolymer, or terpolymer binder) are not cross-linked, for example, by addition of a chemical cross-linking agent. Also, in preferred embodiments, the conductive polymer compositions do not contain a surfactant.

Exemplary ranges for components comprising the dry compositions of the present invention are as follows: about 0.01% to about 5% (of total weight of the dry composition, i.e., without solvent) of a transition metal catalyst, about 50% to about 75% (of total weight of the dry composition, i.e., without solvent) of an electrically conductive material (e.g., graphite), and polymer binder blend or polymer binder of about 15% to about 25% (of total weight of the dry composition, i.e., without solvent), wherein for any combination the total dry weight equals 100%.

The compositions of the present invention may additionally comprise an organic solvent. In one embodiment, the present invention relates to ink compositions comprising between about 0.003% to about 1.6% (of total weight of the composition, including solvent, electrically conductive material, transition metal catalyst, and polymer), preferably about 0.006% to less than 1.6%, more preferably in the range of about 0.03% to about 1.0% (of total weight of the composition, including solvent, electrically conductive material, transition metal catalyst, and polymer) of one or more transition metal catalyst. The ink compositions further comprise one or more electrically conductive materials, a polymer binder blend (or a polymer binder comprising a hydrophilic, acrylic polymer, copolymer, or terpolymer), and one or more solvents. Exemplary ranges for components comprising the ink compositions of the present invention are as follows: about 0.003% to about 1.6% (of total weight of the composition, including solvent, electrically conductive material, transition metal catalyst, and polymer) of a transition metal catalyst, about 15% to about 25% of electrically conductive material (of total weight of the composition, including solvent, electrically conductive material, transition metal catalyst, and polymer) (e.g., graphite), and polymer binder blend (or polymer binder comprising a hydrophilic, acrylic polymer, copolymer, or terpolymer) about 4% to about 8% (of total weight of the composition, including solvent, electrically conductive material, transition metal catalyst, polymer), and an organic solvent about 50% to about 80% (of total weight of the composition, including solvent, electrically conductive material, transition metal catalyst, and polymer), wherein for any ink composition combination the total weight equals 100%.

As is suitable, the catalysts employed in the subject method typically involve the use of metals that can catalyze the oxidation of hydrogen peroxide. In general, any transition metal may be used as the catalyst, such as, for example, a metal selected from one of Groups 3–12 of the periodic table or from the lanthanide series. However, in preferred embodiments, the metal will be selected from the group of late transition metals, preferably from Groups 5–12, more preferably from Groups 8–10, even more preferably from transition metals catalysts. For example, suitable catalysts include, but are not limited to, platinum, palladium, ruthenium, iridium, osmium, and rhodium, as well as mixtures thereof. In a preferred embodiment, the transition metal catalyst is platinum.

The transition metal catalyst is present preferably in the range of between about 0.003% to about 1.6% (of total weight of the composition, including solvent, electrically conductive material, transition metal catalyst, and polymer; before using the composition to create an electrode, for example, by printing). More preferably the catalyst is present in the range of between about 0.03% to about 1.0% (of total weight of the composition, including solvent, electrically conductive material, transition metal catalyst, and polymer).

In general, the transition metal catalysts for use in the invention are obtained from commercial sources and used without further processing. The transition metal catalysts for use in the present composition can be, for example, in the form of a finely divided powder or can be deposited on a solid support, such as graphite or carbon. The transition metal powder preferably possesses high surface area and small particle size. An exemplary metal powder catalyst that is useful in the present invention is platinum black that typically has a surface area of greater than 5 $m^2/g$. In one aspect, the metal powder catalysts have a surface area that is about 5–60 $m^2/g$, or more preferably about 5–30 $m^2/g$. Typically, the particle size of the transition metal powder is typically less than about 50 microns, preferably less than about 20 microns, more preferably less than about 10 microns, and most preferably less than 1 micron.

In another embodiment, the transition metal catalyst is deposited on a solid support prior to use in the composition of the invention. The solid support is preferably a good electrical conductor but inert to electrochemical reaction. Solid supports for use in the invention include, but are not limited to, graphite and carbon. Metal catalysts supported on solids, such as platinum on graphite, can be obtained from commercial sources or prepared by methods known in the art. The metal:solid support ratio is typically in the range of about 10:90 to about 0.5:99.5.

For the preparation of the compositions of the present invention, between about 0.01% to about 5% (of total weight of the dry composition, i.e., without solvent), preferably about 0.05% to less than 5%, more preferably in the range of about 0.1% to about 2% (of total weight of the dry composition, i.e., without solvent) transition metal catalyst, such as metal-on-graphite (for example, platinum-on-graphite), is used to give a total catalyst content of, for example, about 1.0% (e.g., 1 part metal catalyst to 99 parts graphite). Subsequently, a metal catalyst, for example platinum black, may be added to increase the catalyst content up to the final concentration of 5% (e.g., 5 parts metal catalyst to 95 parts graphite). For compositions of less than about 1.0% metal catalyst (e.g., 1 part metal catalyst to 99 parts graphite), metal-on-graphite is typically used as the source of the catalyst.

The compositions of the invention additionally comprise an electrically conductive material. Any electrically conductive material can be used, and the material may also be heat-conductive. The electrically conductive material is preferably a good electrical conductor but inert to electrochemical reaction, for example, graphite and conductive carbon particles can be used. Graphite materials suitable for the compositions of the invention include, but are not limited to, synthetic, pyrolytic, or natural graphite, and are normally obtained from commercial sources or prepared using known methods. For example, synthetic graphite can be made from petroleum coke, pyrolytic graphite can be made from natural gas, or obtained from a commercial source, such as Timrex SFG-15 graphite from Timcal Ltd. in Bodio, Switzerland. Optionally, the graphite material may be purified, such as by a high temperature electro-crystallization process, prior to use. Typically, the electrically conductive material has particles with diameters of about 1–30 microns with average particle diameter in the range of about 6–12 microns.

The compositions of the invention additionally comprise an organic binder. In one aspect the organic binder is a polymer binder blend comprising a first polymer or first polymer mixture, wherein the first polymer or polymers comprising the first polymer mixture have characteristic glass transition temperatures, and a second polymer having a characteristic Tg, wherein the Tg of the first polymer or at least one of the polymers comprising the first polymer mixture is higher than the Tg of said second polymer. The second polymer may also be a second polymer mixture, wherein typically all of the polymers comprising the second polymer mixture each have a characteristic Tg less than the Tg of the first polymer or at least one of the polymers comprising the first polymer mixture. In another aspect, the organic binder is a polymer binder comprising a hydrophilic, acrylic polymer, copolymer, or terpolymer.

The organic binder is preferably a polymeric binder, more preferably a thermoplastic binder. The organic binder, preferably a polymer, is selected such that it provides, for example, a matrix for holding the catalyst and the electrically conductive material together, forms a coating that is scratch resistant, has good adhesion properties, is electrochemically inert, and is soluble in an organic solvent. Without being bound to a particular theory, it is generally believed that a hydrophilic polymeric binder de-wets the graphite particles to a greater extent during drying, thereby increasing the graphite surface that is exposed on the surface of the electrode which consequently exposes the catalyst, such as platinum, deposited onto the graphite. The de-wetting process thereby reduces printing defects and increases the sensitivity of the electrode. Thus, the polymers for use in the methods and compositions of the invention are selected such that they have a high degree of hydrophilicity, to a degree sufficient to provide high sensitivity when formulated into an ink, but retains enough hydrophobicity to provide cohesive strength to the dried printed ink.

The organic binders of the invention are typically polymers. The polymers of the present invention can be prepared from a single monomer or prepared from two or more monomers as block copolymers or by random copolymerization.

In a first aspect, the present invention comprises polymer binder blends comprising a first polymer or first polymer mixture, wherein the first polymer or polymers comprising the first polymer mixture have characteristic glass transition temperatures, and a second polymer having a characteristic Tg, wherein the Tg of the first polymer or at least one of the polymers comprising the first polymer mixture is higher than the Tg of the second polymer. With the proviso that when, in a polymer binder blend, the first polymer (or any polymer of the first polymer mixture) and the second polymer are the same copolymer with different molecular weights (e.g., PMMA), neither the first polymer (or any polymer of the first polymer mixture) nor the second polymer comprise styrene, alkyl styrene, cycloaklystyrene or hydroxystyrene monomers. The first polymer (or first polymer mixture) and the second polymer typically are compatible such that when mixed they are miscible and do not exhibit gross symptoms of segregation in solution. In a related embodiment, the present invention comprises polymer binder blends comprising a first polymer or first polymer mixture, wherein the first polymer or polymers comprising the first polymer mixture have characteristic molecular weights (MW), and a second polymer having a characteristic MW, wherein the MW of the first polymer or at least one of the polymers comprising the first polymer mixture is higher than the MW of the second polymer.

In one embodiment, the polymer binder blend consists essentially of a first polymer and a second polymer. The second polymer may, for example, be an acrylic polymer, copolymer, or terpolymer, for example, a hydrophilic acrylic polymer, copolymer, or terpolymer.

Exemplary first polymer or polymers comprising the first polymer mixture include, but are not limited to, poly (methyl methacrylate), PMMA; poly (styrene methyl methacrylate), PSMMA; poly (styrene acylonitrile), SAN; poly (acylonitrile butadiene styrene), ABS; and other thermoplastic polymers.

Exemplary second polymers include, but are not limited to, poly (methyl methacrylate), PMMA; poly (styrene methyl methacrylate), PSMMA; poly (styrene acylonitrile), SAN; poly (acylonitrile butadiene styrene), ABS; and other thermoplastic polymers.

Further exemplary second polymers include, but are not limited to, acrylic polymer, copolymer, or terpolymer, preferably hydrophilic acrylic polymer, copolymer, or terpolymer. Such hydrophilic, acrylic copolymers or terpolymers may comprises acrylate, methacylate, and/or alkyl methacrylate monomers. Such monomers may further comprises functional groups that are hydrophilic, including, but not limited to, amino, hydroxy, and carboxy functional groups. Such functional groups may be mixed and matched in hydrophilic, acrylic copolymers or terpolymers, for example, hydroxy and carboxy, hydroxy and amino, and amino and carboxy functional groups. In some embodiments, the hydrophilic, acrylic polymer, copolymer, or terpolymer comprises acrylic acid monomers that comprise additional hydrophilic functional groups on the α-carbon of the acrylic acid backbone, β-carbon of the acrylic acid backbone, and/or the pendant carboxyl-group on the α-carbon of the acrylic acid backbone.

Alkyl methacrylate monomers that are useful in the practice of this invention are typically obtained by the reaction of methacrylic acid and alkyl alcohols. The alkylacrylates may, for example, contain from 1 to 8 carbon atoms in the alkyl chain. Representative monomers in this group include, but are not limited to, methyl methacrylate, ethyl methacrylate, tert-butyl methacrylate, butyl methacrylate, isobutyl methacrylate, propyl methacrylate, 2-ethylhexyl methacrylate, isoamyl methacrylate, hexyl methacrylate, octyl methacrylate, cyclohexyl methacrylate, and the like.

The second polymer may, for example, comprise about 0% to about 99% weight, based on the total weight of the second polymer, of moieties resulting from the polymerization of monomers comprising the functional groups with other monomers free of hydroxy, carboxy, and amino functional groups to form copolymers or terpolymers.

In one embodiment, the second polymer comprises monomers having hydrophilic functional groups including, but not limited to, hydroxyalkyl acrylate, hydroxy-alkyl methacrylate, acrylic acid, alkyl acrylic acid, methacrylic acid, carboxyalkyl acrylate, carboxyalkyl methacrylate, amino substituted phenyl acrylate, amino substituted phenyl methacrylate, amino substituted phenylalkyl acrylate, amino substituted phenylalkyl methacrylate, amino substituted phenoxy acrylate, amino substituted phenoxy methacrylate, amino alkyl acrylate, amino alkyl methacrylate, vinylamine acrylate, and vinylamine alkyl acrylate. Amino substituted phenyl or phenoxy monomers may further comprise substituents selected from the group consisting of alkyl, cyano, chloro, bromo, methoxy, nitro and methylthio.

Further, the second polymer may comprise monomers including, but not limited to, hydroxyl alkyl acrylate, hydroxyalkyl methacrylate, acrylic acid, methacrylic acid, carboxyalkyl acrylate, aminoalkyl acrylate, and aminoalkyl methacrylate. Exemplary hydroxyl alkyl acrylate monomers include, but are not limited to 2-hydroxyethyl acrylate, 2-hydroxypropyl acrylate, 3-hydroxypropyl acrylate, 4-hydroxybutyl acrylate, 3,4-dihydroxybutyl acrylate, 2-hydroxyethyl methacrylate, 2-hydroxypropyl ethacrylate, 3-hydroxypropyl methacrylate, 4-hydroxybutyl methacrylate, and 3,4-dihydroxybutyl methacrylate. Exemplary carboxy alkyl acrylate monomers include, but are not limited to carboxymethyl acrylate, 2-carboxyethyl acrylate, 2-carboxypropyl acrylate, 3-carboxypropyl acrylate, 4-carboxybutyl acrylate, carboxymethyl methacrylate, 2-carboxyethyl methacrylate, 3-carboxypropyl methacrylate, and 4-carboxybutyl methacrylate. Exemplary amino substituted acrylate and/or amino substituted alkylacrylate monomers include, but are not limited to ortho substituted aminophenyl acrylate, meta substituted aminophenyl acrylate, para substituted aminophenyl acrylate, amino phenethyl acrylate, amino phenheptyl acrylate, p-amino phenoxy acrylate, 2-(dimethyl amino)ethyl acrylate, 2-(diethylamino) acrylate, 3-(diethylamino)-propyl acrylate, 2-t-butylaminoethyl acrylate, N,N-dibutylaminoethyl acrylate, 2-t-octylaminoethyl acrylate, 7-amino-3,4-dimethyloctyl acrylate, ortho substituted aminophenyl methacrylate, meta substituted aminophenyl methacrylate, para substituted aminophenyl methacrylate, amino phenethyl methacrylate, amino phenheptyl methacrylate, p-amino phenoxy methacrylate, 2-(dimethyl amino)ethyl methacrylate, 2-(diethylamino) methacrylate, 3-(diethylamino)-propyl methacrylate, 2-t-butylaminoethyl methacrylate, N,N-dibutylaminoethyl methacrylate, 2-t-octylaminoethyl methacrylate, and 7-amino-3,4-dimethyloctyl methacrylate. Exemplary vinylamine substituted acrylate and/or vinylamine substituted alkyl acrylate monomers include but are not limited to, vinylamine, N,N-dimethylvinylamine, N,N-diethylvinylamine, N-methyl-N-phenylvinylamine, and N,N-diphenylvinylamine.

Exemplary monomers free of hydroxy, carboxy, and amino functional groups that may be used in the production of hydrophilic, acrylic acid polymers, copolymers, or terpolymers include, but are not limited to, the following monomers: styrene, methyl methacrylate, ethyl methacrylate, propylmethacrylate, isopropyl methacrylate, hexyl methacrylate, 2-ethylhexyl methacrylate, nonyl methacrylate, lauryl methacrylate, stearyl methacrylate, isodecyl methacrylate, ethyl acrylate, methyl acrylate, propyl acrylate, isopropyl acrylate, butyl acrylate, isobutyl acrylate, hexyl acrylate, 2-ethylhexyl acrylate, nonyl acrylate, lauryl acrylate, stearyl acrylate, isodecyl acrylate, ethylene methacrylate, propylene methacrylate, isopropylene methacrylate, butane methacrylate, isobutylene methacrylate, hexene methacrylate, 2-ethylhexene methacrylate, nonene methacrylate, isodecene methacrylate, cyclopentyl acrylate, 4-methyl cyclohexyl acrylate, benzyl methacrylate, o-bromobenzyl methacrylate, phenyl methacrylate, nonylphenyl methacrylate, benzyl acrylate, phenoxy methacrylate, benzyl acrylate, phenyl acrylate, o-bromobenzyl acrylate, nonylphenyl acrylate, phenethyl methacrylate, phenoxyl methacrylate, phenylpropyl methacrylate, nonylphenylethyl methacrylate, phenethyl acrylate, phenoxyl acrylate, phenylpropyl acrylate, nonylphenylethyl acrylate, 2-ethoxyethoxymethyl methacrylate, ethoxyethoxyethyl methacrylate, 2-ethoxyethoxymethyl acrylate, ethoxyethoxyethyl acrylate, glycido methacrylate, 2,3-epoxybutyl methacrylate, 2,3-epoxybutyl acrylate, 3,4-epoxybutyl acrylate, 3,4-epoxybutyl methacrylate, 2,3-epoxypropyl methacrylate, 2,3-epoxypropyl acrylate, 2-methoxyethyl methacrylate, 2-ethoxyethyl methacrylate, 2-butoxyethyl methacrylate, 2-methoxyethyl acrylate, 2-ethoxyethyl acrylate, 2-butoxyethyl acrylate, tetrahydrofurfuryl methacrylate, tetrahydrofurfuryl acrylate, ethoxylated bisphenyl-A-dimethylacrylate, ethylene glycol diacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-methyl-1,6-hexane diol dimethacrylate, diethylene glycol diacrylate, diethylene glycol dimethacrylate, trimethylol propane trimethacrylate tetraethylene glycol diacrylate, tetraethylene glycol dimethacrylate, dipropylene glycol dimethacrylate, trimethylol propyl triacrylate, glycerol triacrylate, glycerol trimethacrylate, pentaerythritol triacrylate, pentaerythritol tetraacrylate, and pentaerythritol tetramethacrylate.

In a second aspect of the present invention, instead of the polymer binder blend, a polymer binding material is used that comprises a hydrophilic acrylic polymer, copolymer, or terpolymer. In one embodiment, the polymer binding material consists essentially of one hydrophilic acrylic polymer, copolymer, or terpolymer. In some embodiments, the hydrophilic, acrylic polymer, copolymer, or terpolymer comprises acrylic acid monomers that comprise additional hydrophilic functional groups on the α-carbon of the acrylic acid backbone, β-carbon of the acrylic acid backbone, and/or the pendant carboxyl-group on the α-carbon of the acrylic acid backbone. Exemplary monomer subunits of hydrophilic, acrylic polymers, copolymer, and terpolymers, as well as specific hydrophilic, acrylic polymers, copolymer, and terpolymers, have been described in detail herein above.

The polymeric binder can be obtained from commercial sources or can be prepared by polymerizing the monomers. The polymer can be prepared by known methods, for example, bulk polymerization, solution polymerization, suspension polymerization, emulsion polymerization, dispersion polymerization and the like. Typically, the polymers are prepared under free radical addition polymerization conditions. These conditions typically involve the gradual addition, frequently over a period of several hours, of a mixture of unreacted monomers and free radical initiators into a solvent solution that is generally maintained at a reaction temperature typically ranging from room temperature to about 200° C. The reaction mixture is typically "chased" after all the monomer has been added by the addition of additional free radical initiator to ensure more complete polymerization. Suitable polymers can be prepared by conducting the reaction in the presence of an ester or ketone, such as n-butyl acetate or methyl amyl ketone in the presence of suitable initiators such as t-butyl perbenzoate, t-butyl peroctoate or azobis(2-methylbutyronitrile). Other useful free radical initiators well known in the art include, but are not limited to, azobis(2-methylbutyronitrile), dipropyl peroxide, di-t-butyl peroxide, cumene hydroperoxide, t-butyl perbenzoate, t-butyl peroctoate and the like. The total amount of initiator used throughout the reaction will typically be from 0.5% to about 10%, preferably about 4% to about 9% by weight of the total monomer charge.

A typical composition of the invention can be prepared by methods known in the art following the guidance of the present specification (e.g., Example 1). Typically, a polymer binder blend or polymer binder solution is prepared by dissolving the polymer binder blend in a suitable solvent.

The methods and compositions of the invention may optionally comprise a solvent. A suitable solvent for use in the composition of the present invention typically has low levels of electrochemically-active impurities (i.e., has low electrochemical activity) in order to maintain low background current, is able to dissolve the polymer binder blend or polymer binder, and has an evaporation rate suitable for electrode printing and production. Typically the solvent is inert to transition metal-catalyzed chemical reactions. Exemplary solvents include, but are not limited to, alkyl and aryl ketones, aromatic hydrocarbons, glycol acetates, glycol diacetates, and mixtures thereof. A preferred glycol diacetate solvent for use in the invention is ethylene glycol diacetate (EGDA). Use of ethylene glycol diacetate, in formulation of a catalyst ink of the present invention, is described in Example 1.

A typical transition metal-graphite composition of the present invention may be prepared as follows. First, a polymer binder blend solution is prepared by dissolving a polymer binder blend, as described herein, in a suitable solvent. Dispersion of the graphite powder and the transition metal-graphite powder in the polymer binder blend solution may be prepared by various mixing techniques, e.g., by roll-milling, high-speed dispersion, or planetary mixing. Additional solvent (e.g., EGDA) may be added to adjust viscosity for optimal deposition. The resulting composition is suitable for deposition, e.g., by screen-printing.

The concentration of the polymer binder blend or polymer binder solution will depend on the solubility of the polymer binder blend or the polymer binder in the solvent. The electrically conductive material, the transition metal catalyst, and, if necessary, more solvent are added to the polymer binder blend or polymer binder solution. The catalyst is normally present at a concentration in the range of between about 0.003% to about 1.6% (of total weight of the composition, including solvent, electrically conductive material, transition metal catalyst, and polymer) transition metal catalyst, preferably about 0.006% to less than 1.6%, more preferably in the range of about 0.03% to about 1.0% (of total weight of the composition, including solvent, electrically conductive material, transition metal catalyst, and polymer) of a transition metal catalyst.

The amount of the electrically conductive material will depend on the type of material chosen, and can be expressed as a ratio of the polymer to the electrically conductive material. When the material is graphite, the ratio of polymer:graphite is, for example, preferably about 1:3 to about 1:5, more preferably about 1:3.5. The resulting mixture is, for example, mixed by hand until a homogeneous mixture is obtained. The mixing process may comprise running the homogeneous mixture through a triple mill, for example, up to 5 times. Additional solvent may be added to adjust the viscosity of the solution before deposition (e.g., by screen printing).

The conductive polymer composition may be deposited on, for example, a non-conductive substrate by a conventional printing process. Exemplary printing processes include, but are not limited to, the following: thick film printing (e.g., screen printing), lithography, letter press printing, vapor deposition, spray coating, ink jet printing, laser jet printing, roller coating, vacuum deposition, and combinations thereof. The non-conductive substrate is typically heat stabilized, prior to deposition of the conducting layers, to confer dimensional stability. Exemplary non-conductive substrates include, but are not limited to, a polyester sheet material, polycarbonate, polyvinyl chloride, high density polypropylene, low density polypropylene. In a preferred embodiment, the non-conductive substrate is a polyester sheet.

After deposition of conductive polymer composition, the polymer binder blend or polymer binder may be stabilized or cured by a number of conventional processes, including, but not limited to, forced air drying (e.g., at elevated temperatures), infra-red irradiation, ultraviolet irradiation, ion-beam irradiation, gamma irradiation, and combinations thereof. These processes typically result, to varying degrees, in the cross-linking of individual molecules of the polymer binder. When ultraviolet radiation is used inclusion of a photo-sensitizing reagent, to initiate the polymer cross-linking reaction, may be desirable to include in the conductive polymer composition.

Example 1 describes the materials used for the formulation of catalyst inks of one aspect of the present invention. In this aspect, the polymer binder blend comprises a first polymer, wherein the first polymer has a characteristic glass Tg, and a second polymer having a characteristic Tg, wherein the Tg of the first polymer is higher than the Tg of the second polymer. In this embodiment the first polymer has a molecular weight greater than the molecular weight of the second polymer. The polymers used in this example were high molecular weight poly (methyl methacrylate) (PMMA) (MW 350,000, Tg 122°) and low molecular weight PMMA (MW 120,000, Tg 114°).

In Example 1, a first medium comprising the high molecular weight PMMA and EGDA was prepared. A second medium comprising the low molecular weight PMMA and EGDA was prepared (high/low molecular weights are relative between the two polymers). The first medium was mixed and stirred under thermostatic temperature controlled condition until a clear polymer solution was obtained. The second medium was then added and stirred under thermostatic temperature controlled condition until a clear polymer solution was obtained.

The polymer binder blend catalyst ink was prepared by the addition of graphite powder (as conductive material), platinum on graphite (as the transition metal catalyst), and the organic solvent EGDA. Two exemplary ink formulations were made, one using 50:50 mixture of the first medium and the second medium, and the second using 70:30 mixture of the first medium and the second medium. Each resulting solution (i.e., ink composition) was mixed until a homogenous mixture was obtained. Each ink formulation was then used to screen print electrodes.

Example 2 provides a comparison of the performance of PMMA polymer binder blend compositions (50:50 ratio and 70:30 as binder) with control polymer binders comprising single polymers. Table 1 shows data obtained from the composition having polymer blend of PMMA with high molecular weight and PMMA with low molecular weight (high and low molecular weight are relatively to each other) at 50:50 ratio and 70:30 as binder, as compared to data obtained from the composition having one polymer (of either the high or low molecular weight PMMA) as binder. The results of these experiments demonstrated that the sensors made from the inks using mixture of polymers with high molecular weight (or high Tg) and low molecular weight (or low Tg) gave substantially lower background current, compared to those from the inks using one PMMA of either high or low molecular weight (control). The overall detection sensitivity, as measured by percent recovery/background current, is improved when PMMA polymer binder blends are used. The inks made from the polymer binder blends showed excellent print quality.

Example 3 describes ink formulations of a second aspect of the present invention. In this example, a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer. In this example, the first polymer mixture was a mixture of high and low molecular weight PMMA. The second polymer was a hydrophilic, acrylic copolymer, exemplified by the following polymers: Poly (styrene/2-ethylhexyl acrylate/methacrylic acid) (Dianal BR-57), Poly (methyl methacrylate/acrylic acid) (Dianal PB-204); Poly (benzyl methacrylate), Poly (4-vinyl phenyl-co-methyl methacrylate), Styrene acrylic polymers with acrylic acid (e.g., Joncryl ECO 675, Joncryl 682), Hydroxy functional acrylic copolymer resin with acrylic acid (GQ806BL60), and poly(hydroxystyrene methyl methacrylate.

Example 4 provides a comparison of the performance of the ink compositions comprising polymer binder blends described in Example 3. Table 2 shows data obtained from the ink composition comprising polymer binder blends (Example 3), as compared to data obtained from a poly (styrene methyl methacrylate) ink composition (control). The experiments performed in support of the present invention indicated that all sensors made from ink formulations using polymer binder blends show significantly lower background current than the control and most sensors made using the polymer binder blends of the present invention showed higher percent recovery relative to the control formulation. The overall sensor detection sensitivity, as measured by recovery/background current, was improved when polymer binder blends of the present invention were used as binder material relative to the use of the single polymer as binder (control).

Example 5 describes ink formulations comprising polymer binder blends wherein poly (styrene methyl methacrylate) is used as the first polymer and a variety of hydrophilic, acrylic copolymers are used as the second polymer.

Example 6 provides a comparison of the performance of the ink compositions comprising polymer binder blends described in Example 5. Table 3 shows data obtained from the ink composition comprising polymer binder blends (Example 3), as compared to data obtained from a poly (styrene methyl methacrylate) ink composition (control). The data presented in Table 3 demonstrate that the sensors made using ink formulations of the present invention comprising polymer binder blends showed better sensor performance (recovery/background current) than the ink formulations using the single binder polymer (control).

Example 7 describes an ink formulation comprising a hydrophilic, acrylic copolymer as a polymer binder for ink composition. The materials used for the catalyst ink formulation included the hydrophilic, acrylic copolymer Dianal PB-204, poly (methyl methacrylate/acrylic acid), MW 9,000, Tg 74.5–77.5° C. The ink formulation was used to print sensors.

Example 8 provides a comparison of the performance of the ink composition of Example 7 to a control ink. A platinum/carbon ink, previously described, was used as control. This control ink results in a sensor having about 5% platinum versus the approximately 1% platinum content of the sensors of the present invention. The data demonstrated that the sensors made from the ink formulation with the hydrophilic, acrylic copolymer binder had extremely high sensitivity compared to the control ink with only slightly higher background current. The overall sensor detection sensitivity, as measured by recovery/background current, was improved with the hydrophilic, acrylic copolymer binder relative to the control ink even though the amount of platinum catalyst in the hydrophilic, acrylic copolymer-based ink (1%) was reduced compared to the control (5%).

The ink compositions of the present invention comprising polymer binder blends offer enhanced screen-printability and result in sensor electrodes with improved detection sensitivity when used in as biosensors in analyte monitoring devices. Experiments performed in support of the present invention indicate that if a copolymer used in the formulation of the polymer binder blends of the present invention is more hydrophilic, e.g. contains acrylic acid, the resulting working electrode shows good detection sensitivity (i.e., lower background current and higher sensitivity).

In one aspect, the conductive polymer compositions of the present invention are used in methods of making electrodes. The present invention also comprises electrodes made using the compositions described herein. For example, the conductive polymer compositions may be deposited as a single electrode, a micro-electrode or as a microelectrode array. The electrode may be used in conjunction with a counter electrode, and a reference electrode deposited on the same substrate. For example, an electrode assembly may be produced by depositing a conductive polymer composition on a non-conducting substrate and depositing a second conducting layer comprising silver/silver chloride, to function as reference and counter electrodes, adjacent to the first layer. One example of such an electrode assembly is a bimodal electrode. In the bimodal electrode configuration the counter electrode (of the "sensor element") and the iontophoretic electrode (of the "sampling mechanism") function non-simultaneously (e.g., as described in U.S. Pat. No. 5,954,685).

Electrodes of the present invention have several characteristics that make their use desirable for measuring low concentrations of analytes (e.g., glucose) including, but not limited to, low background noise electrochemistry (which is particularly important when measuring low levels of electrical current). The electrode composition is formulated using analytical- or electronic-grade reagents and solvents that ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are typically selected for high volatility in order to reduce washing and cure times.

Electrodes of the present invention may be used for the analysis of analytes (or chemical species) that can be directly oxidized or reduced by the removal or addition of electrons at the electrode. The electrodes may also be used to detect analytes (or chemical species) that can be converted by an enzyme to form a product that can be directly oxidized or reduced by the removal or addition of electrons at the electrode. In one embodiment of the present invention, the electrode is derivatized with or held in association with one or more enzymes, e.g., glucose oxidase. In one embodiment, an enzyme is maintained on the electrode in a layer that is separate from but in intimate contact with the reactive surface of the electrode (e.g., as when a hydrogel comprising such enzyme is in contact with the reactive surface of the electrode). The enzyme may also be immobilized on the electrode surface following the guidance of the present specification and employing immobilization methods known in the art.

The present invention comprises methods of producing the conductive polymer compositions and ink compositions described herein. For example, a method of producing a conductive polymer composition of the present invention may comprise mixing a transition metal catalyst, electrically conductive material, polymer, and a suitable solvent to obtain a homogenous mixture, removing the solvent, wherein removing the solvent produces the conductive polymer composition. The present invention also comprises electrodes comprising the conductive polymer compositions, described herein, on a non-conducting substrate. The present invention also comprises methods of making electrodes. For example, a method of making an electrode may comprise mixing a transition metal catalyst, electrically conductive material, polymer, and a suitable solvent to obtain a homogenous mixture, depositing the homogenous mixture on a non-conducting substrate, and removing the solvent to make the electrode. Alternately, an ink composition may be deposited on a non-conducting substrate, and the solvent removed to make the electrode.

3.0 Performance of Analyte Monitoring Devices Using Electrodes of the Present Invention The conductive polymer film compositions and inks described herein may be used, for example, in the manufacturing of sensing electrodes. Such sensing electrodes may be used to detect analyte-related electrochemical signals, for example, when employed in analyte monitoring devices. GlucoWatch biographer glucose monitoring devices (developed and manufactured by Cygnus, Inc., Redwood City, Calif.) have been used as an exemplary electrochemical analyte monitoring device to demonstrate, in tracking studies, the usefulness and benefits of use electrodes formed from the conductive compositions of the present invention. The results of the tracking studies are presented in Examples 9–11.

The tracking study population typically consisted of 8 subjects, females and males, greater than 18 years of age. The Cygnus GlucoWatch G2 biographers used in the tracking study were research versions of the device that were used to collect all of the raw data typically collected by a GlucoWatch G2 biographer; but the device performed no calculations based on the raw data. Emulator programs, which used baseline subtraction and carried out integration of current signal, were used to calculate nanocoulomb (nC) results based on the nanoamp (nA) signals. Although the results are described with reference to the GlucoWatch G2 biographer, the compositions and methods of the present invention may be applied to other analyte monitoring devices as well.

In one aspect of the present invention, a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer (e.g., the formulations described in Example 3). Example 9 describes three tested conditions for a representative ink formulation of this type. Condition 1, Example 9, used a control sensor ink (a previously described platinum/carbon ink, see, e.g., EP 0 942 278 B1, U.S. Pat. No. 6,587,705), with a hydrogel comprising 100 mM phosphate buffer. Iontophoretic extraction was carried out using a current of 0.3 mA/cm$^2$. Current measurements were taken for seven minutes with a biosensor potential of 0.42V. Condition 2 employed a sensing electrode made from one of the ink formulations of the present invention, PMMA 350K/PMMA 120K/PB-204 (see, Examples 3 and 4). A hydrogel comprising 100 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.42V. Condition 3 employed a sensing electrode made from one of the ink formulations of the present invention, PMMA 350K/PMMA 120K/PB-204 (see, Examples 3 and 4). A hydrogel comprising 100 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.33V.

The results obtained from these experiments, performed in support of the present invention, demonstrated that the ink formulations of the present invention (e.g., comprising a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer) are useful for the formulation of sensing electrodes that can be used in the detection of analyte-related electrochemical signal. These sensing electrodes were useful for detection of analyte-related signal even when reduced biosensor potentials were used. Use of lower sensing electrode potentials in analyte monitoring devices employing electrochemical detection may be desirable for the following reasons: (i) such reduced electrode potentials may decrease the contribution of signal related to interfering species on total detected signal; (ii) such reduced electrode potentials may decrease the contribution of signal related to oxidation of the electrode itself on total detected signal; and (iii) such reduced electrode potentials tend to decrease anodal background magnitudes. In addition, experiments performed in support of the present invention indicated that these sensing electrodes provide low baseline, background signals. Such a low background signal coupled with good detection of analyte related signal results in a good signal to noise ratio, that is, good analyte sensitivity of the electrode.

Electrodes having the same composition (i.e., electrodes comprising a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer) were also evaluated after extraction of analyte from subjects using different iontophoretic current densities (Example 10). Two conditions were tested. In Condition 1 (Example 10) the sensing electrode comprised the binder PMMA 350K/PMMA 120K/PB-204. A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.42V. In Condition 2, the sensing electrode comprised the binder PMMA 350K/PMMA 120K/PB-204. A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.1 mA/cm$^2$. Current measurements were taken for seven minutes with a biosensor potential of 0.42V.

The results of these experiments demonstrated that the ink formulations of the present invention (e.g., comprising a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer) are useful for the formulation of sensing electrodes used in the detection of analyte-related electrochemical signal (e.g., glucose-related electrochemical signals). One advantage of sensing electrodes of the present invention, as demonstrated by Example 10, is the ability to use reduced iontophoretic current density for analyte extraction without compromising the analyte sensitivity of the electrode. Two related benefits to employing reduced iontophoretic current density in an analyte monitoring device are potential reduction of skin irritation and reduced energy consumption requirements for analyte monitoring devices that employ iontophoretic extraction, possibly resulting in further miniaturization of such devices.

In another aspect, the present invention relates to the use of hydrophilic, acrylic copolymers as a polymer binder for ink compositions (see, e.g., Examples 7 and 8). One exemplary hydrophilic, acrylic copolymer is PB-204. Electrodes printed using the PB-204 ink of the present invention described in Example 7 (see also Example 8) were used in tracking studies (Example 11) to confirm the usefulness and benefits of electrodes printed using this ink composition of the present invention. Three tested conditions (Example 11) were as follows. In Condition 1, a control sensor ink was used (previously described platinum/carbon ink, see, e.g., EP 0 942 278 B1, U.S. Pat. No. 6,587,705). A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.42V. In Condition 2, the electrode comprised PB-204 as the binder. A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.42V. In Condition 3, the electrode comprised PB-204 as the binder. A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.33V. In Condition 4, the electrode comprised PB-204 as the binder. A hydrogel comprising 200 mM phosphate buffer acted as an ionically conductive medium for iontophoretic extraction and collection reservoir for analyte. The hydrogel was in contact with the sensing electrode as well as the iontophoretic electrodes. Iontophoretic extraction was carried out using a current of 0.3 mA/cm$^2$. Current measurements were taken for seven minutes with a biosensor potential of 0.25V.

These results demonstrate that the ink formulations of the present invention, comprising binders comprising hydrophilic acrylic copolymer (e.g., PB-204) are useful for the formulation of sensing electrodes used in the detection of analyte-related electrochemical signal. These data illustrate the usefulness and benefits of these electrodes even when reduced biosensor potentials are used. Advantages of employing reduced biosensor potentials were discussed above. In addition, experiments performed in support of the present invention indicated that sensing electrodes, comprising binders comprising hydrophilic acrylic copolymer, provide low background, baseline signals, and provide excellent signal to noise ratios.

The results of these experiments demonstrate the value of the conductive polymer film compositions, inks, and electrodes of the present invention for use in analyte monitoring devices in a clinical environment (i.e., the tracking studies).

Although a number of methods and materials similar or equivalent to those described herein can be used in the practice of the present invention, some preferred materials and methods are described herein.

Experimental

The following examples are put forth so as to provide those of ordinary skill in the art with a complete disclosure and description of how to make and use the devices, methods, and formulae of the present invention, and are not intended to limit the scope of what the inventor regards as the invention. It is also to be understood that the terminology used herein is for the purpose of describing particular embodiments of the invention only, and is not intended to be limiting. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Formulation of a 1.0% Catalyst Ink

The materials used for the following catalyst ink formulations (Example 1) were as follows:

22.42 g high molecular weight poly (methyl methacrylate) (PMMA) medium 2 (12.5% in EGDA, MW 350,000, Tg 122°; Aldrich, Milwaukee, Wis.);

11.21 g low molecular weight PMMA medium 1(25.0% in EGDA, MW 120,000, Tg 114°; Aldrich);

37.10 g EGDA;

20.63 g graphite (Timrex SFG-1 5, Timcal Ltd., Bodio, Switzerland); and 5.5 g platinum on graphite (5% platinum, Johnson-Matthey, Royston, UK).

12.5% PMMA (high MW) in EGDA was prepared by mixing one part PMMA (MW: 350,000) and seven parts EGDA. 25.0% PMMA (low MW) in EGDA was prepared by mixing one part PMMA (MW: 120,000) and three parts EGDA.

Two polymer binding solutions were prepared as follows:

Medium 1. 62.5 grams of PMMA (MW: 350,000) was added into a water-jacketed glass container, then 437.5 grams of EGDA was added. The resulted mixture was stirred under thermostatic temperature controlled condition at 80° C. for 8 hours, a clear polymer solution was obtained.

Medium 2. 125grams of PMMA (MW: 120,000) was added into a water-jacketed glass container, then 375 grams of EGDA was added. The resulted mixture was stirred under thermostatic temperature controlled condition at 80° C. for 8 hours, a clear polymer solution was obtained.

A 50:50 polymer binder blend (ratio of higher MW, higher Tg polymer, i.e., medium 1, to lower MW, lower Tg polymer, i.e., medium 2; wherein the ratio is given as weight percent of the total polymer in the polymer binder blend) was prepared as follows. The polymer binder blend catalyst ink was prepared as follows. 22.42 grams of polymer medium 1 and 11.21 grams of polymer medium 2 were added to plastic jar. 20.63 grams of graphite powder Timrex SFG 15 and 5.5 grams of platinum, 5% on graphite were then added to the jar. 37.10 grams of EGDA were then added. The resulting solution was mixed by hand until a homogenous mixture was obtained. After a viscous, uniform dispersion was obtained that was free of large particles, the jar was covered with a lid and rolled on the roller for at least 8 hours.

A 70:30 polymer binder blend (ratio higher MW, higher Tg polymer, i.e., medium 1, to lower MW, lower Tg polymer, i.e., medium 2) was prepared in a similar manner. The polymer binder blend catalyst ink was prepared as follows. 31.39 grams of polymer medium 1 and 6.73 grams of polymer medium 2 were added to plastic jar. 20.63 grams of graphite powder Timrex SFG 15 and 5.5 grams of platinum, 5% on graphite were then added to the jar. 37.10 grams of EGDA were then added. The resulting solution was mixed by hand until a homogenous mixture was obtained. After a viscous, uniform dispersion was obtained that was free of large particles, the jar was covered with a lid and rolled on the roller for at least 8 hours.

The jar of ink was kept rolling on a jar roller to maintain dispersion of the ingredients and to prevent settling. Ink screen-printing was performed using a 180 mesh stainless steel screen and a 90 durometer squeegee. The 1.0% catalyst ink formulation was 1 part platinum to 99 parts graphite. With solvent the weight percent of platinum in the catalyst ink formulation was about 0.2705%. After printing and drying the weight percent of platinum in the printed electrode was about 0.874%.

EXAMPLE 2

Comparison of Sensor Performance Using the Inks of Example 1

The performance of PMMA polymer binder blend compositions (50:50 ratio and 70:30 ratio used as binder) were compared. Table 1 shows data obtained from the composition having polymer blend of PMMA with high molecular weight and PMMA with low molecular weight (high and low molecular weight are relatively to each other) at 50:50 ratio and 70:30 as binder, as compared to data obtained from the composition having one polymer (of either the high or low molecular weight PMMA) as binder. In these formulations, the platinum content was kept constant (1.0%) and all from platinum on graphite (5% platinum, Johnson-Matthey), and graphite content and total percent binder are also kept the same. The results of functional tests at two different temperatures are given.

TABLE 1

| Ink formulation Description | 24° C. | | | 32° C. | | |
| --- | --- | --- | --- | --- | --- | --- |
| | BG (nA) | 2.5 min. % R | 10 min. % R | BG (nA) | 2.5 min. % R | 7 min. % R |
| PMMA Mw 120,000 low Tg (control) | 94 | 46 | 85 | 137 | 76 | 104 |
| PMMA Mw 350,000 high Tg (control) | 168 | 42 | 84 | 106 | 71 | 101 |
| PMMA 50:50 (high:low) | 83 | 43 | 86 | 112 | 68 | 97 |
| PMMA 70:30 (high:low) | 81 | 44 | 89 | 85 | 55 | 91 |

The data in Table 1 were obtained by placing the printed sensor in contact with a hydrogel electrolyte, and pipetting a known amount a solution of glucose to the surface of the hydrogel. The hydrogel was approximately 7 mil (175 microns) thick and contained glucose oxidase enzyme to oxidize glucose, producing hydrogen peroxide as a product. A wicking material was placed onto the surface of the hydrogel to facilitate spreading of the glucose solution over the surface of the hydrogel. This technique was performed at two different temperatures, 24° C. and 32° C.

In this procedure, the biosensor was biased, and the background allowed to come to equilibrium for one hour. Ten microliters of 0.2 mM glucose were pipetted onto the wick on the surface of the gel. The current from the biosensor was measured for 50 minutes. The current was integrated over time. The percentage of the total theoretical charge recovered in 2.5 minutes and 10 minutes (for the 24° C test) or 2.5 minutes and 7 minutes (for the 32° C. test) was calculated, and reported as a measure of the sensitivity of the electrode. A high-sensitivity electrode will exhibit high percent recoveries at the 2.5 minute time point, approaching 100% recovery by the 7 minute mark (for the 32° C. test).

In Table 1, the first column presents information on the polymer binder composition of the ink formulation, the second column shows the background (BG) current measured in nanoamps performed at 24° C., the third column shows the percent recovery (% R) at 2.5 minutes performed at 24° C., the fourth column shows the percent recovery at 10 minutes performed at 24° C., the fifth column shows the background (BG) current measured in nanoamps performed at 32° C., the sixth column shows the percent recovery at 2.5 minutes performed at 32° C., and the seventh column shows the percent recovery at 7 minutes performed at 32° C.

The sensors made from the inks using mixture of polymers with high molecular weight (or high glass transition temperature) and low molecular weight (or low glass transition temperature) gave substantially lower background current, compared to those from the inks using one PMMA of either high or low molecular weight (control). The percent recovery was essentially the same. Accordingly, the overall signal to noise ratio, as measured by percent recovery/ background current, was improved when PMMA polymer blend was used relative to a single PMMA polymer.

The ink made from higher molecular weight PMMA gave much better print quality than that from lower molecular weight PMMA. The print was uniform and showed a clean edge, i.e., no bleed effect was observed. The inks made from the polymer binder blends also showed excellent print quality.

The inks in this example exemplified a polymer binder blend comprising a first polymer, wherein the first polymer has a characteristic glass transition temperature, and a second polymer having a characteristic Tg, wherein the Tg of the first polymer is higher than the Tg of the second polymer. Further, in this example, the first polymer has a characteristic molecular weight (MW), and the second polymer has a characteristic MW, wherein the MW of the first polymer was greater than the MW of the second polymer.

EXAMPLE 3

Mixture of High MW PMMA and Low MW PMMA As Polymer A and Low Molecular Weight Acrylic Copolymer as Polymer B The materials used as exemplary polymer B's for the following catalyst ink formulations (Example 3) were as follows:

Dianal BR-57: Poly (styrene/2-ethylhexyl acrylate/methacrylic acid); MW 40,000; Tg 58.6–61.5° C.; styrene>75% (Dianal America, Inc., Pasadena, Tex.);

Dianal PB-204: Poly (methyl methacrylate/acrylic acid); MW 9,000; Tg 74.5–77.5° C. (Dianal America, Inc.);

Poly (benzyl methacrylate): MW 70,000; Tg 54° C. (Aldrich);

Poly (4-vinyl phenyl-co-methyl methacrylate): MW 10,100; Tg 102° C. (Aldrich);

Joncryl ECO 675: Styrene acrylic polymers with acrylic acid; MW 5,700; Tg 103° C. (Johnson Polymer, Sturtevant, Wis.);

Joncryl 682: Styrene acrylic polymers with acrylic acid; MW 1,700; Tg 56° C. (Johnson Polymer);

Joncryl 680: MW 4,900; Tg 67° C. (Johnson Polymer);

GQ806BL60: Hydroxy functional acrylic copolymer resin with acrylic acid; Tg 47° C. (Cognis, Cincinatti, Ohio);

Poly (hydroxystyrene methyl methacrylate) (Aldrich).

With reference to Example 4, Table 2, for the formulations of Second Polymer indicated by a superscript 1, the ink compositions were formulated as follows: Medium 1 (25% polymer) and Medium 2 (12.5% polymer) were prepared as described in Example 1. The polymer binder blend catalyst ink was prepared as follows: 22.42 grams of polymer medium 1 and 11.21 grams of polymer medium 2 were added to plastic jar (a 50:50 ratio, based on weight percent of the polymers in this blend). Then 20.63 grams of graphite powder Timrex SFG 15 and 5.5 grams of platinum, 5% on graphite were added. Followed by 31.21 grams of EGDA. The resulting solution was mixed by hand until a homogenous mixture was obtained. After a viscous, uniform dispersion was obtained that was free of large particles, the jar was covered with a lid and rolled on the roller for at least 8 hours. Then, 6.35 g of 25% PB-204 was added to the mixture and stirred using a plastic spatula by hand until a uniform dispersion was obtained.

The polymer binder blend comprising poly (benzyl methacrylate) was prepared essentially as just described, except 10.48 g of 12.5% poly (benzyl methacrylate) in EGDA was added before the addition of the 20.63 g of graphite powder and PB-204 was not added.

With reference to Example 4, Table 2, for the formulations of Second Polymer indicated by a superscript 2, the ink compositions were formulated as follows. First, 22.42 grams of polymer medium 1 and 11.21 grams of polymer medium 2 were added to plastic jar (a 50:50 ratio, weight percent of polymers in this blend). Then 20.63 grams of graphite powder Timrex SFG 15 and 5.5 grams of platinum, 5% on graphite were added followed by 38.0 grams of EGDA. The resulting solution was mixed by hand until a homogenous mixture was obtained. After a viscous, uniform dispersion was obtained that was free of large particles, the jar was covered with a lid and rolled on the roller for at least 8 hours. Then, to 20 g of this mixture, 1.3 g of 25% PB-204 in EGDA, or 1.3 g of 25% Joncryl 675 in EGDA, or 1.3 g of 25% Joncryl 682 in EGDA, was added and stirred using a plastic spatula by hand until a uniform dispersion was obtained.

With reference to Example 4, Table 2, for the formulations of Second Polymer indicated by a superscript 3, the ink compositions were formulated as follows. First, 33.63 g of 12.5% solution of PMMA (MW 270K) was added to plastic jar. Then 20.63 grams of graphite powder Timrex SFG 15 and 5.5 grams of platinum, 5% on graphite were added followed by 23.24 grams of EGDA were added. The resulting solution was mixed by hand until a homogenous mixture was obtained. After a viscous, uniform dispersion was obtained that was free of large particles, the jar was covered with a lid and rolled on the roller for at least 8 hours. Then to 20 g of this mixture, 2.8 g of 25% poly (hydroxystyrene methyl methacrylate) in EGDA, or 2.8 g of 25% Joncyl 680 in EGDA, or 1.2 g of 60% GQ806BL60 in EGDA, was added and stirred using a plastic spatula by hand until a uniform dispersion was obtained.

With reference to Example 4, Table 2, for the formulations of Second Polymer indicated by a superscript 4, the ink compositions were formulated as follows: 22.42 grams of 12.5% PMMA 270K in EGDA and 11.21 grams of 25% PMMA 120K were added to plastic jar (a 50:50 ratio, weight percent of these two polymers). Then 20.63 grams of graphite powder Timrex SFG 15 and 5.5 grams of platinum, 5% on graphite were added followed by 35.0 grams of EGDA. The resulting solution was mixed by hand until a homogenous mixture was obtained. After a viscous, uniform dispersion was obtained that was free of large particles, the jar was covered with a lid and rolled on the roller for at least 8 hours. Then, 1.0 g of 25% PB-204 in EGDA, or 0.42 g of 60% GQ806BL60 in EGDA, was added to the mixture and stirred using a plastic spatula by hand until a uniform dispersion was obtained.

For all formulations, the jar of ink was kept rolling on a jar roller to maintain dispersion of the ingredients and to prevent settling. Ink screen-printing was performed using a 180 mesh stainless steel screen and a 90 durometer squeegee. The 1.0% catalyst ink formulation was 1 part platinum to 99 parts graphite. With solvent the weight percent of platinum in the catalyst ink formulation was about 0.2705%. After printing and drying the weight percent of platinum in the printed electrode was about 0.85%.

The ink formulations described in this example used high MW PMMA and low MW PMMA as polymers comprising the first polymer mixture and a low molecular weight acrylic copolymer as the second polymer (high and low molecular weights are relative to each other). All Second Polymers, as listed in the examples of Second Polymers (Example 4, Table 2), have glass transition temperature lower than the high MW PMMA.

EXAMPLE 4

Comparison of Sensor Performance Using the Inks of Example 3

A previously described platinum/carbon (wherein the carbon was graphite) ink was used as control (see, e.g., EP 0 942 278 B1, U.S. Pat. No. 6,587,705). This control results in a sensor having about 5% platinum versus the approximately 1% platinum content of the sensors of the present invention. Because the catalytic inks described in Example 3 were prepared at different times and the resulting sensors were tested in different groups at different times, each group has a separate control with which it was compared (in Table 2, below, each group follows a Control Ink heading). The fact that the data from the control varies somewhat from time to time does not adversely affect the results of the present study, because data are only compared within group. Comparisons of sensors was carried out essentially as described above in Example 2.

TABLE 2

| First Polymer | Second Polymer | BG (nA) | 24° C. 2.5 min % R | 10 min % R |
|---|---|---|---|---|
| Control Ink | | 92.3 | 30.5 | 74.3 |
| PMMA 350K/PMMA 120K (50:50) | Poly(benzyl methacrylate)[1] | 67.3 | 36.0 | 82.9 |
| PMMA 350K/PMMA 120K (50:50) | PB-204[2] | 64.3 | 40.1 | 85.5 |
| PMMA 350K/PMMA 120K (50:50) | Joncryl 675[2] | 67.2 | 25.2 | 72.9 |
| PMMA 350K/PMMA 120K (50:50) | Joncryl 682[2] | 66.5 | 33.1 | 79.7 |
| Control Ink | | 110 | 28.2 | 73.3 |
| PMMA MW 270 | Poly(hydroxystyrene methyl methacrylate)[3] | 95 | 34.6 | 82.1 |
| PMMA MW 270 | Joncyl 680[3] | 71 | 33.4 | 81.4 |
| PMMA MW 270 | GQ806BL60[3] | 71 | 33.4 | 81.4 |
| Control Ink | | 83.3 | 24.5 | 68.1 |
| PMMA 270K/PMMA 120K (50:50) | PB-204[4] | 72.3 | 35.2 | 80.8 |
| PMMA 270K/PMMA 120K (50:50) | GQ806BL60[4] | 51.2 | 25.1 | 71.7 |
| Control Ink | | 92.5 | 25.5 | 69.1 |
| PMMA 350K/PMMA 120K (50:50) | PB-204[1] | 69 | 35.5 | 79.9 |

(Table 2, superscripts 1–4 are described in Example 3.)

In Table 2, the first column presents the first polymer or polymers comprising the first polymer mixture for the ink formulation, the second column presents information on the second polymer composition of polymer binder blend composition, the third column shows the background (BG) current measured in nanoamps performed at 24° C., the fourth column shows the percent recovery (% R) at 2.5 minutes performed at 24° C., and the fifth column shows the percent recovery at 10 minutes performed at 24° C.

The above data show that all sensors made from ink formulations using polymer binder blends show significantly lower background current and most sensors made using the polymer binder blends of the present invention show higher percent recovery relative to the control formulation. The overall sensor detection sensitivity, as measured by recovery/background current, was improved when polymer binder blends of the present invention were used as binder material relative to the use of single polymers as binder (control).

This example illustrates both a polymer binder blend comprising (i) a first polymer mixture, wherein the polymers comprising the first polymer mixture have characteristic glass transition temperatures, and a second polymer having a characteristic Tg, wherein the Tg of at least one of the polymers comprising the first polymer mixture is higher than the Tg of the second polymer; and (ii) a first polymer, wherein the the first polymer has a characteristic glass transition temperature, and a second polymer having a characteristic Tg, wherein the Tg of the first polymer is higher than the Tg of the second polymer.

EXAMPLE 5

PSMMA Used as the First Polymer

The materials used as exemplary first polymer for the following catalyst ink formulations (Example 5) were as follows:

PSMMA (poly (styrene methyl methacrylate), MW 100K–150K, Tg 101° C. (Aldrich).

The materials used as exemplary second polymer for the following catalyst ink formulations (Example 5) were as follows:

Dianal PB-204: Poly (methyl methacrylate/acrylic acid); MW 9,000; Tg 74.5–77.5° C. (Dianal America, Inc.);

PMMA: MW 15,000, Tg 114° C. (Aldrich).

The first polymer was prepared by dissolving PSMMA in EGDA to make a 25% solution. The polymer binder catalyst ink was prepared as follows. First, 24.6 grams of 25% PSMMA in EGDA was added to plastic jar. Then 20.63 grams of graphite powder Timrex SFG 15 and 5.5 grams of platinum, 5% on graphite were added followed by 49.7 grams of EGDA. The resulting solution was mixed by hand until a homogenous mixture was obtained. After a viscous, uniform dispersion was obtained that was free of large particles, the jar was covered with a lid and rolled on the roller for at least 8 hours. Then, as the second polymer, either 2.0 grams of 15.9% PB-204 in EGDA or 1.0 g of 29.4% PMMA in EGDA was added to 20 g of the homogenous mixture and stirred using a plastic spatula by hand until a uniform dispersion was obtained.

The jar of ink was kept rolling on a jar roller to maintain dispersion of the ingredients and to prevent settling. Ink screen-printing was performed using a 180 mesh stainless steel screen and a 90 durometer squeegee. The 1.0% catalyst ink formulation was 1 part platinum to 99 parts graphite. With solvent the weight percent of platinum in the catalyst ink formulation was about 0.2705%. After printing and drying the weight percent of platinum in the printed electrode was about 0.85%.

The ink formulations described in this example used PSMMA as the first polymer and a low molecular weight acrylic polymer or copolymer as the second polymer (high and low molecular weights are relative to each other). Both the PB-204 and the PMMA used in this example (see also Table 3) have glass transition temperature lower than the PSMMA.

EXAMPLE 6

Comparison of Sensor Performance Using the Inks of Example 5

Comparisons of sensors were carried out essentially as described above in Example 2.

TABLE 3

| Ink formulation | | 24° C. | | | 32° C. | | |
|---|---|---|---|---|---|---|---|
| First Polymer | Second Polymer | BG (nA) | 2.5 min. % R | 10 min. % R | BG (nA) | 2.5 min. % R | 7 min. % R |
| PSMMA (control) | — | 106 | 34 | 88 | 67 | 54 | 91 |
| PSMMA | PB-204 | 81 | 30 | 78 | 66 | 63 | 94 |
| PSMMA | PMMA | 64 | 29 | 79 | 73 | 61 | 95 |

The PSMMA control ink was formulated as described above, except the second polymer was not added.

In Table 3, the first column presents the first polymer used for the ink formulation, the second column presents the second polymer used in the ink formulation, the third column shows the background (BG) current measured in nanoamps performed at 24° C., the fourth column shows the percent recovery (% R) at 2.5 minutes performed at 24° C., the fifth column shows the percent recovery at 10 minutes performed at 24° C., the sixth column shows the background (BG) current measured in nanoamps performed at 32° C., the seventh column shows the percent recovery at 2.5 minutes performed at 32° C., and the eighth column shows the percent recovery at 7 minutes performed at 32° C.

The data presented above demonstrate that the sensors made using ink formulations of the present invention comprising polymer binder blends showed better sensor performance (recovery/background current) than the ink formulation using a single binder polymer PSMMA (control).

EXAMPLE 7

Use of Hydrophilic, Acrylic Copolymer as Polymer Binder in 1.0% Catalyst Ink Formulation The materials used for the following catalyst ink formulation (Example 7) were as follows:

24.6 g polymer medium: Dianal PB-204: Poly (methyl methacrylate/acrylic acid); MW 9000; Tg 74.5–77.5° C. (Dianal America, Inc., Pasadena, Tex.); 25% in EGDA;

20.3 g graphite powder (Timrex SFG-15, Timcal Ltd., Bodio, Switzerland);

5.41 g platinum-on-graphite catalyst (5% platinum, Johnson-Matthey, Royston, UK);

49.7 g ethylene glycol diacetate (EGDA).

The polymer medium was prepared as follows: 125 grams of Dianal PB-204 powder was added into a water-jacketed glass container, then 375 grams of EGDA was added. The resulting mixture was stirred under thermostatic temperature-controlled condition at 80° C. for 9 hours until a clear polymer solution was obtained.

The ink was prepared as follows: 24.6 grams of the polymer medium was added to a plastic jar. Then 20.3 g graphite powder Timrex SFG-15 and 5.41 g platinum-on-graphite catalyst were added to the jar followed by 49.7 g of EGDA. The resulting solution was mixed by hand until a homogenous mixture was obtained. After a viscous, uniform dispersion was obtained that was free of large particles, the jar was covered with a lid and rolled on the roller for at least 8 hours.

The jar of ink was kept rolling on a jar roller to maintain dispersion of the ingredients and to prevent settling. Ink screen-printing was performed using a 180 mesh stainless steel screen and a 90 durometer squeegee. The 1% catalyst ink formulation was 1 part platinum to 99 parts graphite. With solvent the weight percent of platinum in the catalyst ink formulation was about 0.2705%. After printing and drying, the weight percent of platinum in the printed electrode was about 0.85%.

EXAMPLE 8

Comparison of Sensor Performance Using the Inks of Example 7

The performance of the ink formulation described in Example 7 was compared to a control ink. A previously described platinum/carbon (wherein the carbon was graphite) ink was used as control (see, e.g., EP 0 942 278 B1, U.S. Pat. No. 6,587,705). This control ink provided a sensor having about 5% platinum versus the approximately 1% platinum content of the sensors of the present invention.

Table 4 shows data obtained from the composition having the Dianal PB-204 polymer binder compared to the control ink by the method described above in Example 2.

TABLE 4

| Ink Formulation | BG (nA) | 2.5 min % R | 10 min % R |
|---|---|---|---|
| Control Ink | 97 | 24.1 | 66.5 |
| PB-204-based ink | 121 | 52.5 | 86.7 |

In Table 4, the first column presents an arbitrary name designation for the ink formulation, the second column shows the background (BG) current measured in nanoamps performed at 24° C., the third column shows the percent recovery (% R) at 2.5 minutes performed at 24° C., and the fourth column shows the percent recovery at 10 minutes performed at 24° C.

The above data demonstrated that the sensors made from the ink formulation with the PB-204 binder had extremely high sensitivity (% R) compared to the control ink with only slightly higher background current. The overall sensor detection sensitivity, as measured by recovery/background current, was improved with the PB-204 binder relative to the control ink even though the amount of platinum catalyst in the PB-204-based ink was reduced compared to the control (1% for the PB-204 ink vs. 5% for the control ink).

This example illustrates a conductive polymer composition comprising a transition metal catalyst, an electrically conductive material; and a polymer binder comprising a hydrophilic, acrylic copolymer.

EXAMPLE 9

Tracking Studies and Results Concerning Performance of Electrodes of the Present Invention Using Different Biosensor Electrode Potentials Electrodes printed using the PMMA 350K/PMMA 120K/PB-204 ink of the present invention described in Examples 3 and 4 (see, e.g., Example 4, Table 2) were used in tracking studies to confirm the usefulness and benefits of electrodes printed using this ink composition of the present invention. These electrodes exemplified the use of a polymer binder blend comprising a first polymer mixture, wherein polymers comprising the first polymer mixture have characteristic Tg's, and a second polymer having a characteristic Tg, wherein the Tg of at least one of the polymers comprising the first polymer mixture is higher than the Tg of the second polymer. The tested conditions included the following:

Condition 1: Sensor Ink (Control)—a previously described platinum/carbon (wherein the carbon was graphite) ink was used as control (see, e.g., EP 0 942 278 B1, U.S. Pat. No. 6,587,705), Hydrogel—100 mM phosphate buffer. Iontophoretic extraction was carried out using a current of 0.3 mA/cm$^2$. Current measurements were taken for seven minutes with a biosensor potential of 0.42V.

Condition 2: PMMA 350K/PMMA 120K/PB-204 Sensor Ink, Hydrogel—100 mM phosphate buffer. Iontophoretic extraction was carried out using a current of 0.3 mA/cm$^2$. Current measurements were taken for seven minutes with a biosensor potential of 0.42V.

Condition 3: PMMA 350K/PMMA 120K/PB-204 Sensor Ink, Hydrogel—100 mM phosphate buffer. Iontophoretic extraction was carried out using a current of 0.3 mA/cm$^2$. Current measurements were taken for seven minutes with a biosensor potential of 0.33V.

The tracking study population consisted of 8 subjects (all subjects greater than 18 years old). GlucoWatch G2 biographers, providing each of the above-described conditions, were applied to each subject on lower and upper arm sites and run for approximately 15 hours. Two GlucoWatch G2 biographers were applied to each subject for each condition. Each subject fasted for 1.5 hours prior to administration of the GlucoWatch G2 biographer. Fingerprick blood measurements were taken two per hour (at 55 and 15 minute points, except at elapsed time 1:15) from elapsed time (ET) 0:55 through 2:55, three per hour (at 15, 35, and 55 minute points) from ET 3:15 through 4:55, two per hour (at 15 and 35 minute points) from ET 5:15 through 5:35, two per hour (at 15 and 55 minute points) from ET 6:15 through 6:55, and one per hour (at 55 minute points) from ET 7:55 through 13:55. Reference blood measurements were taken 20 minutes prior to the corresponding biographer measurement to account for 20 minutes of lag time. Reference blood measurements (including fingerprick blood measurements) were taken using a One Touch® Ultra (LifeScan, Inc., Milpitas, Calif.) blood glucose meter.

The GlucoWatch G2 biographers were research versions of the device that were used to collect all of the raw data typically collected by a GlucoWatch G2 biographer; but the device performed no calculations based on the raw data, for example, the device did not calculate a glucose measurement value. Accordingly, glucose readings were not provided to the users. The raw data from the research GlucoWatch G2 biographers were stored to a data file called MLOG. Exemplary data saved to the MLOG file included, but was not limited to, elapsed time, temperature data, first sensor current readings (in nanoamps), second sensor current readings. Further information concerning MLOG can be found, for example, in U.S. Pat. No. 6,633,772. The MLOG data allowed for various analyses to be performed. Statistical analyses were performed on the data using a number of standard software packages.

These analyses differ from those generally performed on GlucoWatch G2 biographer data in that they focused primarily on GlucoWatch G2 biographer nanoamp signal. Emulator programs, employing baseline subtraction and integration (see, e.g., U.S. Pat. No. 6,233,471), were used to calculate nanocoulomb results based on the nanoamp signals. As part of the standard analysis, the 2-hour point was used as the 1$^{st}$ point to produce nC regression tables. Average background values were temperature corrected with respect to the expected value at calibration (CAL time; ET 2:15) and calculated using previous baseline subtraction. Analysis of Variance (ANOVA) was performed for correlation coefficients. Least squares nC slope and intercept values for ET2:00–15:00 were calculated.

The coefficient of determination ($R^2$), least squares slope (nC/mg/dL), and least squares intercept (nC) are presented for unscreened nC data, for ET 2:00–9:00, in Table 5. The nC readings were based on readings from both sensors of the GlucoWatch G2 biographer for a given measurement cycle (i.e., sensor A+sensor B).

TABLE 5

| Condition | | $R^2$ | Least Squares Slope | Least Squares Intercept |
|---|---|---|---|---|
| 1: Control: Standard Sensor ink, biosensor potential of 0.42 V | Average | 0.51 | 150 | 996 |
| | Standard Deviation | 0.30 | 137 | 9395 |
| 2: PMMA 350K/PMMA 120K/PB-204 Sensor Ink, biosensor potential of 0.42 V | Average | 0.60 | 156 | −1273 |
| | Standard Deviation | 0.21 | 82 | 8045 |
| 3: PMMA 350K/PMMA 120K/PB-204 Sensor Ink, biosensor potential of 0.33 V | Average | 0.59 | 111 | −3524 |
| | Standard Deviation | 0.25 | 60 | 4568 |

From the data presented in Table 5 several important conclusions may be drawn. The most relevant pair-wise comparisons for the data in Table 5 are between conditions 1 and 2. This pair-wise condition used the same biosensor potential for detection of nanoamp signal. Comparison of $R^2$ results showed consistent results for all conditions, including the reduced biosensor potential of condition 3. Comparison of the least squares slopes showed a consistent result for all conditions.

These results demonstrated that the ink formulations of the present invention (for example, comprising a polymer binder blend comprising a first polymer mixture, wherein polymers comprising the first polymer mixture have characteristic Tg, and a second polymer having a characteristic Tg, wherein the Tg of at least one of the polymers comprising the first polymer mixture is higher than the Tg of the second polymer, e.g., mixtures of high/low molecular weight PMMA and a low molecular weight acrylic copolymer) are useful for the formulation of sensing electrodes used in the detection of analyte-related electrochemical signal, even when reduced biosensor potentials are used. Use of lower sensing electrode potentials may be desirable because they decrease the effect of interfering species on detected signal and they tend to decrease anodal background magnitudes. Further, such reduced electrode potentials may decrease the contribution of signal related to oxidation of the electrode itself on total detected signal. In addition, experiments performed in support of the present invention indicated that sensing electrodes, comprising mixtures of high/low molecular weight PMMA and a low molecular weight acrylic copolymer, provide low baseline signals, which results in a good signal to noise ratio (i.e., good analyte sensitivity).

EXAMPLE 10

Tracking Studies and Results Concerning Performance of Electrodes of the Present Invention Using Different Iontophoretic Current Densities Electrodes printed using the PMMA 350K/PMMA 120K/PB-204 ink of the present invention described in Examples 3 and 4 (see, e.g., Example 4, Table 2) were used in tracking studies to confirm the usefulness and benefits of electrodes printed using this ink composition of the present invention. These electrodes exemplify use of a polymer binder blend comprising a first polymer mixture, wherein polymers comprising the first polymer mixture have characteristic Tg's, and a second polymer having a characteristic Tg, wherein the Tg of at least one of the polymers comprising the first polymer mixture is higher than the Tg of the second polymer. The tested conditions included the following:

Condition 1: PMMA 350K/PMMA 120K/PB-204 Sensor Ink, Hydrogel—200 mM phosphate buffer. Iontophoretic extraction was carried out using a current of 0.3 mA/cm$^2$. Current measurements were taken for seven minutes with a biosensor potential of 0.42V.

Condition 2: PMMA 350K/PMMA 120K/PB-204 Sensor Ink, Hydrogel—200 mM phosphate buffer. Iontophoretic extraction was carried out using a current of 0.1 mA/cm$^2$. Current measurements were taken for seven minutes with a biosensor potential of 0.42V.

The tracking study population consisted of 8 subjects (all subjects greater than 18 years old). GlucoWatch G2 biographers, providing each of the above-described conditions, were applied to each subject on lower and upper arm sites and run for approximately eight hours. Two GlucoWatch G2 biographers were applied to each subject for each condition. Each subject fasted for 1.5 hours prior to administration of the GlucoWatch G2 biographer. Fingerprick blood measurements were taken two per hour (at 55 and 15 minute points) from elapsed time (ET) 0:55 through 3:15, three per hour (at 15, 35, and 55 minute points) from ET 3:15 through 5:35, and two per hour (at 15 and 55 minute points) from ET 5:55 through 7:55. Reference blood measurements were taken 20 minutes prior to the corresponding biographer measurement to account for 20 minutes of lag time. Reference blood measurements (including fingerprick blood measurements) were taken using a One Touch® Ultra (LifeScan, Inc., Milpitas, Calif.) blood glucose meter. Oral glucose was taken by the subjects at ET 3:15.

The GlucoWatch G2 biographers were research versions of the device that were used to collect all of the raw data typically collected by a GlucoWatch G2 biographer, as described in Example 9. Data manipulation was also carried out as described in Example 9.

The coefficient of determination ($R^2$), least squares slope (nC/mg/dL), and least squares intercept (nC) are presented for unscreened nC data, for ET 2:00–8:00, in Table 6. The nC readings were based on readings from both sensors of the GlucoWatch G2 biographer for a given measurement cycle (i.e., sensor A+sensor B).

TABLE 6

| Condition | | $R^2$ | Least Squares Slope | Least Squares Intercept |
|---|---|---|---|---|
| 1: Control: PMMA 350K/PMMA 120K/PB-204 Sensor Ink, Iontophoretic extraction current 0.3 mA/cm$^2$. | Average Standard Deviation | 0.52 0.24 | 380 180 | −9669 16666 |
| 2: PMMA 350K/PMMA 120K/PB-204 Sensor Ink, Iontophoretic extraction current 0.1 mA/cm$^2$. | Average Standard Deviation | 0.60 0.20 | 162 55 | −1346 5537 |

From the data presented in Table 6 several important conclusions may be drawn. Comparison of $R^2$ results showed consistent results for both conditions, including the reduced iontophoretic extraction current of condition 2. Comparison of the least squares slopes showed a consistent result for both conditions.

These results demonstrated that the ink formulations of the present invention (for example, electrodes comprising a polymer binder blend comprising a first polymer mixture, wherein polymers comprising the first polymer mixture have characteristic Tg's, and a second polymer having a characteristic Tg, wherein the Tg of at least one of the polymers comprising the first polymer mixture is higher than the Tg of the second polymer, e.g., mixtures of high/low molecular weight PMMA and a low molecular weight acrylic copolymer) are useful for the formulation of sensing electrodes used in the detection of analyte-related electrochemical signal. Further, these results demonstrate that the sensing electrodes made from these ink formulations had good analyte sensitivity, as evidenced by the similar results obtained when using an iontophoretic extraction current of 0.3 mA/cm$^2$ and a lower iontophoretic extraction current of 0.1 mA/cm$^2$. One advantage of sensing electrodes made from these ink formulations of the present invention is the ability to use reduced iontophoretic current density for analyte extraction without compromising the analyte sensitivity of the electrode. For example, two such benefits of using reduced iontophoretic current density are reduction of skin irritation and reduced energy consumption requirements for analyte monitoring devices employing iontophoretic extraction.

EXAMPLE 11

Tracking Studies and Results Concerning Performance of an Electrode of the Present Invention, Comprising a Hydrophilic Acrylic Copolymer, Using Different Biosensor Electrode Potentials Electrodes printed using the PB-204 ink of the present invention described in Example 7 (see also Example 8) were used in tracking studies to confirm the usefulness and benefits of electrodes printed using this ink composition of the present invention. The tested conditions included the following:

Condition 1: Sensor Ink (Control)—a previously described platinum/carbon (wherein the carbon was graphite) ink was used as control (see, e.g., EP 0 942 278 B1, U.S. Pat. No. 6,587,705), Hydrogel—200 mM phosphate buffer. Iontophoretic extraction was carried out using a current of 0.3 mA/cm$^2$. Current measurements were taken for seven minutes with a biosensor potential of 0.42V.

Condition 2: PB-204 Sensor Ink, Hydrogel—200 mM phosphate buffer. Iontophoretic extraction was carried out using a current of 0.3 mA/cm$^2$. Current measurements were taken for seven minutes with a biosensor potential of 0.42V.

Condition 3: PB-204 Sensor Ink, Hydrogel—200 mM phosphate buffer. Iontophoretic extraction was carried out using a current of 0.3 mA/cm$^2$. Current measurements were taken for seven minutes with a biosensor potential of 0.33V.

Condition 4: PB-204 Sensor Ink, Hydrogel—200 mM phosphate buffer. Iontophoretic extraction was carried out using a current of 0.3 mA/cm$^2$. Current measurements were taken for seven minutes with a biosensor potential of 0.25V.

The tracking study population consisted of 8 subjects (all subjects greater than 18 years old). GlucoWatch G2 biographers, providing each of the above-described conditions, were applied to each subject on lower and upper arm sites and run for approximately 8 hours. Two GlucoWatch G2 biographers were applied to each subject for each condition. Each subject fasted for 1.5 hours prior to administration of the GlucoWatch G2 biographer. Fingerprick blood measurements were taken two per hour (at 55 and 15 minute points) from elapsed time (ET) 0:55 through 3:15, three per hour (at 15, 35, and 55 minute points) from ET 3:15 through 5:35, and two per hour (at 15 and 55 minute points) from ET 5:55 through 7:55. Reference blood measurements were taken 20 minutes prior to the corresponding biographer measurement to account for 20 minutes of lag time. Reference blood measurements (including fingerprick blood measurements) were taken using a One Touch® Ultra (LifeScan, Inc., Milpitas, Calif.) blood glucose meter. Oral glucose was taken by the subjects at ET 3:15.

The GlucoWatch G2 biographers were research versions of the device that were used to collect all of the raw data typically collected by a GlucoWatch G2 biographer, as described in Example 9. Data manipulation was also carried out as described in Example 9.

The coefficient of determination ($R^2$), least squares slope (nC/mg/dL), and least squares intercept (nC) are presented for unscreened nC data, for ET 2:00–8:00, in Table 7. The nC readings were based on readings from both sensors of the GlucoWatch G2 biographer for a given measurement cycle (i.e., sensor A+sensor B).

TABLE 7

| Condition | | $R^2$ | Least Squares Slope | Least Squares Intercept |
|---|---|---|---|---|
| 1: Control: Standard Sensor ink, biosensor potential of 0.42 V | Average Standard Deviation | 0.56 0.20 | 330 103 | −6971 9971 |
| 2: PB-204 Sensor Ink, biosensor potential of 0.42 V | Average Standard Deviation | 0.62 0.23 | 387 132 | −6131 10887 |
| 3: PB-204 Sensor Ink, biosensor potential of 0.33 V | Average Standard Deviation | 0.64 0.15 | 352 110 | −9148 7575 |
| 4: PB-204 Sensor Ink, biosensor potential of 0.25 V | Average Standard Deviation | 0.60 0.17 | 221 74 | −6920 3852 |

From the data presented in Table 7 several important conclusions may be drawn. First, comparison of $R^2$ results showed consistent results for all conditions, including the reduced biosensor potentials of conditions 3 and 4. Second, comparison of the least squares slopes showed a consistent result for all conditions.

These results demonstrated that the ink formulations of the present invention, comprising binders comprising hydrophilic acrylic copolymer (e.g., PB-204), are useful for the formulation of sensing electrodes used in the detection of analyte-related electrochemical signal, even when reduced biosensor potentials are used. As discussed above, use of lower sensing electrode potentials may be desirable because they decrease the effect of interfering species on detected signal and they tend to decrease anodal background magnitudes. In addition, experiments performed in support of the present invention indicated that sensing electrodes, comprising binders comprising hydrophilic acrylic copolymer, provided low baseline signals, which resulted in a good signal to noise ratio (i.e., good analyte sensitivity). For example, the data suggested that either 0.42V or 0.33V may be good choices for sensing electrode potential, using these electrodes of the present invention, because they provided good analyte-related signal to background signal ratios (i.e., they provided good analyte-related signal and low background signal values).

As is apparent to one of skill in the art, various modification and variations of the above embodiments can be made without departing from the spirit and scope of this invention. Such modifications and variations are within the scope of this invention.

What is claimed is:

1. A conductive polymer composition comprising:
   about 0.01% to about 5% by weight of a transition metal catalyst;
   an electrically conductive material; and
   a polymer binder blend comprising a first polymer and a second polymer, wherein the first polymer and the second polymer are selected from the group consisting of: acrylic homopolymers, acrylic copolymers, and acrylic terpolymers, wherein the glass transition temperature of said first polymer is higher than the glass transition temperature of said second polymer, the first polymer, and the second polymer having different molecular weights.

2. The composition of claim 1, wherein said polymer binder blend comprises acrylic homopolymers prepared from polymerized monomers selected from the group consisting of: methyl methacrylate, ethyl methacrylate, tert-butyl methacrylate, butyl methacrylate, isobutyl methacrylate, propyl methacrylate, 2-ethylhexyl methacrylate, isoamyl methylacrylate, and octyl methacrylate.

3. The composition of claim 1, wherein the first polymer is poly (methyl methacrylate) and the second polymer is poly (methyl methacrylate).

4. The composition of claim 3, wherein a ratio said first polymer, or said first polymer mixture, and said second polymer, based on the total weight of polymers in the polymer binder blend is from 80:20 to 40:60.

5. The composition of claim 1, wherein the transition metal catalyst is selected from the group consisting of platinum, palladium, and rhodium.

6. The composition of claim 1, wherein the catalyst comprises platinum on graphite.

7. The composition of claim 1, wherein said polymer, binder blend is a 50:50 blend of poly (methyl methacrylate), homopolymers.

8. The composition of claim 1, wherein said polymer binder blend comprises acrylic copolymers prepared from polymerized monomers is selected from the group consisting of: acrylic acid, methacrylic acid, methyl methacrylate, ethyl methacrylate, propyl methacrylate, isopropyl methacrylate, hexyl methacrylate, 2-ethylhexyl methacrylate, nonyl methacrylate, lauryl methacrylate, stearyl methacrylate, isodecyl methacrylate, ethyl acrylate, methyl acrylate, propyl acrylate, isopropyl acrylate, butyl acrylate, isobutyl acrylate, hexyl acrylate, 2-ethylhexyl acrylate, nonyl acrylate, lauryl acrylate, stearyl acrylate, isodecyl acrylate, ethylene methacrylate, propylene methacrylate, isopropylene methacrylate, butane methacrylate, isobutylene methacrylate, hexene methacrylate, 2-ethylhexene methacrylate, nonene methacrylate, isodecene methacrylate, cyclopentyl acrylate, 4-methyl cyclohexyl acrylate, benzyl methacrylate, o-bromobenzyl methacrylate, phenyl methacrylate, nonylphenyl methacrylate, benzyl acrylate, phenoxy methacrylate, benzyl acrylate, phenyl acrylate, o-bromobenzyl acrylate, nonylphenyl acrylate, phenethyl methacrylate, phenoxyl methacrylate, phenylpropyl methacrylate, nonylphenylethyl methacrylate, phenethyl acrylate, phenoxyl acrylate, phenylpropyl acrylate, nonylphenylethyl acrylate, 2-ethoxyethoxymethyl methacrylate, ethoxyethoxyethyl methacrylate, 2-ethoxyethoxymethyl acrylate, ethoxyethoxyethyl acrylate, glycido methacrylate, 2,3-epoxybutyl methacrylate, 2,3-epoxybutyl acrylate, 3,4-epoxybutyl acrylate, 3,4-epoxybutyl methacrylate, 2,3-epoxypropyl methacrylate, 2,3-epoxypropyl acrylate, 2-methoxyethyl methacrylate, 2-ethoxyethyl methacrylate, 2-butoxyethyl methacrylate, 2-methoxyethyl acrylate, 2-ethoxyethyl acrylate, 2-butoxyethyl acrylate, tetrahydrofurfuryl methacrylate, tetrahydrofurfuryl acryate, ethoxylated bisphenyl-A-dimethylacrylate, ethylene glycol diacrylate, 1,2-prooane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-methyl-1,6-hexane diol dimethacrylate, diethylene glycol diacrylate, diethylene glycol dimethacrylate, trimethylol propane trimethacrylate tetraethylene glycol diacrylate, tetraethylene glycol dimethacrylate, dipropylene glycol dimethacrylate, trimethylol propyl triacrylate, glycerol triacrylate, glycerol trimethacrylate, pentaerythritol triacrylate, pentaerythritol tetraacrylate, and pentaerythritol tetramethacrylate.

9. The composition of claim 1, wherein said polymer binder blend comprises acrylic terpolymers prepared from monomers selected from the group consisting of: methyl methacrylate, ethyl methacrylate, propyl methacrylate, isopropyl methacrylate, hexyl methacrylate, 2-ethylhexyl methacrylate, nonyl methacrylate, lauryl methacrylate, stearyl methacrylate, isodecyl methacrylate, ethyl acrylate, methyl acrylate, propyl acrylate, isopropy acrylate, butyl acrylate, isobutyl acrylate, hexyl acrylate, 2-ethylhexyl acrylate, nonyl acrylate, lauryl acrylate, stearyl acrylate, isodecyl acrylate, ethylene methacrylate, propylene methacrylate, isopropylene methacrylate, butane methacrylate, isobutylene methacrylate, hexene methacrylate, 2-ethylhexene methacrylate, nonene methacrylate, isodecene methacrylate, cyclopentyl acrylate, 4-methyl cyclohexyl acrylate, benzyl methacrylate, o-bromobenzyl methacrylate, phenyl methacrylate, nonylphenyl methacrylate, benzyl acrylate, phenoxy methacrylate, benzyl acrylate, phenyl acrylate, o-bromobenzyl acrylate, nonylphenyl acrylate, phenethyl methacrylate, phenoxyl methacrylate, phenylpropyl methacrylate, nonylphenylethyl methacrylate, phenethyl acrylate, phenoxyl acrylate, phenylpropyl acrylate, nonylphenylethyl acrylate, 2-ethoxyethoxymethyl methacrylate, ethoxyethoxyethyl methacrylate, 2-ethoxyethoxymethyl acrylate, ethoxyethoxyethyl acrylate, glycido methacrylate, 2,3-epoxybutyl methacrylate, 2,3-epoxybutyl acrylate, 3,4-epoxybutyl acrylate, 3,4-epoxybutyl methacrylate, 2,3epoxypropyl methacrylate, 2,3-epoxypropyl acrylate, 2-methoxyethyl methacrylate, 2-ethoxyethyl methacrylate, 2-butoxyethyl methacrylate, 2-methoxyethyl acrylate, 2-ethoxyethyl acrylate, 2-butoxyethyl acrylate, tetrahydrofurfuryl methacrylate, tetrahydrofurfuryl acrylate, ethoxylated bisphenyl-A-dimethylacrylate, ethylene glycol diacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-methyl-1,6-hexane diol dimethacrylate, diethylene glycol diacrylate, diethylene glycol dimethacrylate, trimethylol propane trimethacrylate tetraethylene glycol diacrylate, tetraethylene glycol dimethacrylate, dipropylene glycol dimethacrylate, trimethylol propyl triacrylate, glycerol triacrylate, glycerol trimethacrylate, pentaerythritol triacrylate, pentaerythritol tetraacrylate, and pentaerythritol tetramethacrylate.

10. The composition of claim 1, wherein the polymer binder blend comprises acrylic polymers, copolymers, or terpolymers (i) that are hydrophilic and (ii) are prepared from polymerized acrylic acid monomers that comprise additional hydrophilic functional groups on the alpha-carbon of the acrylic acid backbone, beta-carbon of the acrylic acid backbone, the pendant carboxyl-group on the alpha-carbon of the acrylic acid backbone, or combinations thereof.

11. The composition of claim 1, wherein the conductive material is selected from the group consisting of synthetic graphite, pyrolytic graphite, and natural graphite.

12. An electrode comprising the conductive polymer composition of claim 1 on a non-conducting substrate.

13. A conductive polymer composition comprising:
about 0.01% to about 5% by weight of a transition metal catalyst;
an electrically conductive material; and
a polymer binder blend comprising a first polymer mixture and a second polymer, wherein the first polymer mixture is a mixture of acrylic homopolymers having different glass transition temperatures and different molecular weights and the second polymer is selected from the group consisting of acrylic copolymers and acrylic terpolymers.

14. The composition of claim 13, wherein the first polymixture is a mixture of poly (methyl methacrylate) homopolymers and the second polymer is selected from the group consisting of: styrene, methyl methacrylate, ethyl methacrylate, propyl methacrylate, isopropyl methacrylate, hexyl methacrylate, 2-ethylhexyl methacrylate, nonyl methacrylate, lauryl methacrylate, stearyl methacrylate, isodecyl methacrylate, ethyl acrylate, methyl acrylate, propyl acrylate, isopropyl acrylate, butyl acrylate, isobutyl acrylate, hexyl acrylate, 2-ethylhexyl acrylate, nonyl acrylate, lauryl acrylate, stearyl acrylate, isodecyl acrylate, ethylene methacrylate, propylene methacrylate, isopropylene methacrylate, butane methacrylate, isobutylene methacrylate, hexene methacrylate, 2-ethylhexene methacrylate, nonene methacrylate, isodecene methacrylate, cyclopentyl acrylate, 4-methyl cyclohexyl acrylate, benzyl methacrylate, o-bromobenzyl methacrylate, phenyl methacrylate, nonylphenyl methacrylate, benzyl acrylate, phenoxy methacrylate, benzyl acrylate, phenyl acrylate, o-bromobenzyl acrylate, nonylphenyl acrylate, phenethyl methacrylate, phenoxyl methacrylate, phenylpropyl methacrylate, nonylphenylethyl methacrylate, phenethyl acrylate, phenoxyl acrylate, phenylpropyl acrylate, nonylphenylethyl acrylate, 2-ethoxyethoxymethyl methacrylate, ethoxyethoxyethyl methacrylate, 2-ethoxyethoxymethyl acrylate, ethoxyethoxyethyl acrylate, glycido methacrylate, 2,3-epoxybutyl methacrylate, 2,3-epoxybutyl acrylate, 3,4-epoxybutyl acrylate, 3,4-epoxybutyl methacrylate, 2,3-epoxypropyl methacrylate, 2,3-epoxypropyl acrylate, 2-methoxyethyl methacrylate, 2-ethoxyethyl methacrylate, 2-butoxyethyl methacrylate, 2-methoxyethyl acrylate, 2-ethoxyethyl acrylate, 2-butoxyethyl acrylate, tetrahydrofurfuryl methacrylate, tetrahydrofurfuryl acrylate, ethoxylated bisphenyl-A-dimethylacrylate, ethylene glycol diacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-methyl-1,6-hexane diol dimethacrylate, diethylene glycol diacrylate, diethylene glycol dimethacrylate, trimethylol propane trimethacrylate tetraethylene glycol diacrylate, tetraethylene glycol dimethacrylate, dipropylene glycol dimethacrylate, trimethylol propyl triacrylate, glycerol triacrylate, glycerol trimethacrylate, pentaerythritol triacrylate, pentaerythritol tetraacrylate, and pentaerythritol tetramethacrylate.

15. The composition of claim 13, wherein the transition metal catalyst is selected from the group consisting of platinum, palladium, and rhodium.

16. The composition of claim 13, wherein the catalyst comprises platinum on graphite.

17. The composition of claim 13, wherein said second polymer is selected from the group consisting of: hydroxyl alkyl acrylate, hydroxyl alkyl methacrylate, acrylic acid, methacrylic acid, carboxyalkyl acrylate, aminoalkyl acrylate, aminoalkyl methacrylate, 2-hydroxyethyl acrylate, 2-hydroxypropyl acrylate, 3-hydroxypropyl acrylate, 4-hydroxybutyl acrylate, 3,4-dihydroxybutyl acrylate, 2-hydroxyethyl methacrylate, 2-hydroxypropyl ethacrylate, 3-hydroxypropyl methacrylate, 4-hydroxybutyl methacrylate, 3,4-dihydroxybutyl methacrylate, carboxymethyl acrylate, 2-carboxyethyl acrylate, 2-carboxypropyl acrylate, 3-carboxypropyl acrylate, 4-carboxybutyl acrylate, carboxymethyl methacrylate, 2-carboxyethyl methacrylate, 3-carboxypropyl methacrylate, and 4-carboxybutyl methacrylate, ortho substituted aminophenyl acrylate, meta substituted aminophenyl acrylate, para substituted aminophenyl acrylate, amino phenethyl acrylate, amino phenheptyl acrylate, p-amino phenoxy acrylate, 2-(dimethyl amino)ethyl acrylate, 2-(diethylamino) acrylate, 3-(diethylamino)-propyl acrylate, 2-t-butylaminoethyl acrylate, N,N-dibutylaminoethyl acrylate, 2-t-octylaminoethyl acrylate, 7-amino-3,4-dimethyloctyl acrylate, ortho substituted aminophenyl methacrylate, meta substituted aminophenyl methacrylate, para substituted aminophenyl methacrylate, amino phenethyl methacrylate, amino phenheptyl methacrylate, p-amino phenoxy methacrylate, 2-(dimethyl amino)ethyl methacrylate, 2-(diethylamino) methacrylate, 3-(diethylamino)-propyl methacrylate, 2-t-butylaminoethyl methacrylate, N,N-dibutylaminoethyl methacrylate, 2-t-octylaminoethyl methacrylate, 7-amino-3,4-dimethyloctyl methacrylate, vinylamine substituted acrylate, vinylamine substituted alkyl acrylate, vinylamine acrylates, N,N-dimethylvinylamine acrylates, N,N-diethylvinylamine acrylates, N-methyl-N-phenylvinylamine acrylates, and N,N-diphenylvinylamine acrylates.

18. The composition of claim 13, wherein a ratio of the first polymer mixture to the second polymer is from 80:20 to 40:60, based on the total weight of the polymers in the polymer binder blend.

19. The composition of claim 13, wherein the conductive material is selected from the group consisting of synthetic graphite, pyrolytic graphite, and natural graphite.

20. An electrode comprising the conductive polymer composition of claim 13 on a non-conducting substrate.

21. A conductive polymer composition comprising:
about 0.01% to about 5% by weight of a transition metal catalyst;
an electrically conductive material; and
a polymer binder comprising acrylic copolymers or acrylic terpolymer prepared by polymerizing monomers selected from the group consisting of: alkyl acrylates, alkyl methacrylates, hydroxyl-alkyl acrylates, hydroxyl-alkyl methacrylates, acrylic acid, methacrylic acid, carboxyl alkyl acrylates, carboxyl methacrylates, amino alkylate acrylate, amino alkyl methacrylate, vinylamine acrylate and vinyl amine alkyl acrylate.

* * * * *